US008592151B2

(12) United States Patent
Spinale et al.

(10) Patent No.: US 8,592,151 B2
(45) Date of Patent: Nov. 26, 2013

(54) ASSESSING LEFT VENTRICULAR REMODELING VIA TEMPORAL DETECTION AND MEASUREMENT OF MICRORNA IN BODY FLUIDS

(75) Inventors: Francis G. Spinale, Charleston, SC (US); Michael R. Zile, Charleston, SC (US); Robert E. Stroud, Mt. Pleasant, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 249 days.

(21) Appl. No.: 12/944,670

(22) Filed: Nov. 11, 2010

(65) Prior Publication Data

US 2011/0117560 A1 May 19, 2011

Related U.S. Application Data

(60) Provisional application No. 61/261,774, filed on Nov. 17, 2009.

(51) Int. Cl.
*C12Q 1/68* (2006.01)
(52) U.S. Cl.
USPC .......................................... 435/6.1; 435/6.11
(58) Field of Classification Search
None
See application file for complete search history.

(56) References Cited

U.S. PATENT DOCUMENTS

| 3,817,837 | A | 6/1974 | Rubinstein et al. |
| 3,850,752 | A | 11/1974 | Schuurs et al. |
| 3,939,350 | A | 2/1976 | Kronick et al. |
| 3,996,345 | A | 12/1976 | Ullman et al. |
| 4,275,149 | A | 6/1981 | Litman et al. |
| 4,277,437 | A | 7/1981 | Maggio et al. |
| 4,366,241 | A | 12/1982 | Tom et al. |
| 4,376,110 | A | 3/1983 | David et al. |
| 4,452,901 | A | 6/1984 | Gordon et al. |
| 5,424,000 | A | 6/1995 | Winicov et al. |
| 2004/0121343 | A1 | 6/2004 | Buechler et al. |
| 2009/0005336 | A1 | 1/2009 | Wang et al. |
| 2010/0010073 | A1 | 1/2010 | Thum et al. |
| 2010/0267804 | A1 | 10/2010 | Port et al. |
| 2011/0117560 | A1 | 5/2011 | Spinale et al. |

FOREIGN PATENT DOCUMENTS

| WO | 2007133905 | 11/2007 |
| WO | 2008008809 | 1/2008 |

OTHER PUBLICATIONS

Chapman et al, Am. J. Physiol. heart Circ. Physiol. 286: H1-H10 (2004).*
Kalousova et al, Nephrol. Dial. Transplant. 22: 2020-2026 (2007).*
Absi, et al., "Altered patterns of gene expression distinguishing ascending aortic aneurysms from abdominal aortic aneurysms: Complementary DNSA expression profiling in the molecular characterization of aortic disease", J Thorac Cardiovasc Surg., 126(2):344-57 (2003).
Ahmed, et al., "Matrix metalloproteinases/tissue inhibitors of metalloproteinases: Relationship between changes in proteolytic determinants of matrix composition and structural, functional and clinical manifestations of hypertensive heart desease" , Circ., 113:2089-96 (2006).
Aime-Sempe, et al., "Myocardial cell death in fibrillating and dilated human right atria", J Am College of Cardiology, 34:1577-86 (1999).
Albinsson, et al., "MicroRNAs are necessary for vascular smooth muscle growth, differentiation, and function", Arterioscler Thromb Vase Biol., 30(6):1118-26 (2010).
Alla, et al., "Early changes in serum markers od cardiac extra-cellular matrix turnover in patients with uncomplicated hypertension and type II diabetes", Eur J Heart Fail., 8(2):147-53 (2006).
Allessie, et al., "Electrical, contractile and structural remodeling during atrial fibrillation" , Cardiovasc Res, 54;230-40 (2002).
Allessie, et al., "Pathophysiology and prevention of atrial fibrillation", Circ.,103:769-77 (2001).
Altieri, et al. "Metalloproteinases 2 and 9 are increased in plasma of patients with heart failure", Eur J of Clin Invest, 33:648-56 (2003).
Ambros, et al., "MicroRNAs and other tiny endogenous RNAs in *C. elegans*", Curr. Biol., 13(10):807-18 (2003).
Anderson, et al., "High resolution two-dimensional electrophoresis of human plasma proteins", PNAS, 74:5421-5 (1977).
Ausma, et al., "Reverse structural and gap-junctional remodeling after prolonged atrial fibrillation in the goat", Circulation, 107:2051-8 (2003).
Ausma, et al., "Structural changes of atrial myocardium due to sustained atrial fibrillation in the goat", Circulation, 96:3157-63 (1997).
Ausma, et al., "Time course of atrial fibrillation-induced cellular structural remodeling in atria of the goat", J Mol Cell Cardiol, 33:2083-94 (2001).
Baker, et al., "Metalloproteinase inhibitors: biological actions and therapeutic opportunities", J Cell Sci., 1115 (Pt 19):3719-27 (2002).
Bartel, "MicroRNAs: genomics, biogenesis, mechanism, and function", Cell, 116(2):281-97 (2004).
Bartel, "MicroRNAs: target recognition and regulatory functions", Cell, 136(2):215-33 (2009).
Benjamin, et al., "Impact of atrial fibrillation on the risk of death: the Framingham Heart Study", Circulation, 98:946-52 (1998).
Bigg, et al., "Tissue inhibitor of metalloproteinase-4 inhibits but does not support the activation of gelatinase A via efficient inhibition of membrane type 1-matrix metalloproteinase" , Cancer Res, 61(9):3610-8 (2001).
Blankenberg, et al., "Plasma Concentrations and Genetic Variation of Matrix Metalloproteinase 9 and Prognosis of Patients With Cardiovascular Disease", Circulation, 107:1579-85 (2003).
Boldt, et al., "Fibrosis in left atrial tissue of patients with atrial fibrillation with and without underlying mitral valve disease", Heart, 90:400-05 (2004).
Bollmann, et al., "Atrial fibrillatory frequency predicts atrial defibrillation threshold and early arrhythmia recurrence in patients undergoing internal cardioversion of persistent atrial fibrillation", Pacing Clin Electrophysiol , 25:1179-84 (2002).
Borden, et al., "Transcriptional control of matrix metalloproteinases and the tissue inhibitors of matrix metalloproteinases", Crit Rev Eukaryot Gene Exp, 7:159-78 (1997).

(Continued)

Primary Examiner — James Martinell
(74) Attorney, Agent, or Firm — Meunier Carlin & Curfman, LLC

(57) ABSTRACT

Disclosed are methods and materials for assessing cardiac failure, cardiac hypertrophy, and left ventricular remodeling using microRNA levels. The level of microRNAs can be measured in a body fluid, such as plasma and serum.

19 Claims, 19 Drawing Sheets

(56) References Cited

OTHER PUBLICATIONS

Borges, et al., "Tissue diffusion and retention of metalloproteinases in ascending aortic aneurysms and dissections", Human pathology., 40(3):306-13 (2009).

Boyum, et al., "Matrix metalloproteinase activity in thoracic aortic aneurysms associated with bicuspid and tricuspid aortic valves", J Thorac Cardiovasc Surg., 127(3):686-91(2004).

Bradham, et al., "Differential release of matrix metalloproteinases (MMP\s) and tissue inhibitors of matrix metalloproteinases (TIMP\s) in patients following alcohol induced myocardial infarction", J Am Coil Cardiol, 40(12):2165-73 (2002).

Brew, et al., "Tissue inhibitors of metalloproteinases: evolution,structure and function", Biochim Biophys Acta., 1477:267-83 (2000).

Brundel, et al., "Molecular mechanisms of remodeling in human atrial fibrillation", Cardiovascular Res, 54:315-24 (2002).

Butler, "Enzyme-linked immunosorbent assay", Structure of Antigens, vol. 1 (Van Oss, et al. (eds.) Immunochem, Marcel Dekker, Inc., New York, 1994, 759-803 (1994).

Butler, "The amplified ELISA; principles of and applications for the comparative quantitation of class and subclass antibodies and the distribution of antibodies and antigens in biochemical separates", Methods Enzymol., 73:482-523 (1981).

Butler, "The behavior of antigens and antibodies immobilized on a solid phase", Structure of Antigens, vol. 1 (Van Regenmortel, M., CRC Press, Boca Raton, 209-59 (1992).

Caterina, et al., "Glycosylation and NH2-terminal domain mutant of tissue inhibitor of metalloproteinases-1 (TIMP-1)". Biochem Biophys Acta, 1388: 21-34 (1998).

Chareonthaitawee, et al., "Relation of initial infarct size to extent of left ventricular remodeling in the year after acute myocardial infarction", J Am Coil Cardiol, 25:567-73 (1995).

Chen, et al., "Characterization of microRNAs in serum: a novel class of biomarkers for diagnosis of cancer and other diseases", Cell Res., 18:997-1006 (2008).

Chobanian, et al., National Heart, Lung, and Blood Institute Joint National Committee on Prevention, Detection, Evaluation, and Treatment of High Blood Pressure; National High Blood Pressure Education Program Coordinating Committee. The Seventh Report of the Joint National Committee on Prevention, Detection, Evaluation, and Treatment of High Blood Pressure; the JNC 7 report. JAMA. 2003;289:2560-72.

Chung, et al., "Loss of elastic fiber Integrity and reduction of vascular smooth muscle contraction resulting from the upregulated activities of matrix metalloproteinase-2 and -9 in the thoracic aortic aneurysm in Marfan syndrome", Circ Res.,101(5):512-22 (2007).

Coker, et al., "Matrix metalloproteinase expression and activity in isolated LV myocyte preparations following neurohormonal stimulation", Am J Physiol, 281:H543-H551 (2001).

Creemers, et al., "Deficiency of TIMP-1 exacerbates LV remodeling after myocardial infarction in mice", Am J Physiol, 284:H364-371 (2002).

Creemers, et al., "Matrix Metalloproteinase Inhibition After Myocardial Infarction. A new approach to prevent heart failure", Circulation Res, 89;201-210 (2001).

Damodarasamy, et al., "Collagen Extracts Derived From Young and Aged Mice Demonstrate Different Structural Properties and Cellular Effects in Three-Dimensional Gels", J Gerontol A Biol Sci Med Sci., 65(3):209-18 (2010).

Deisenhofer, et al., "Circumferential mapping and electric isolation of pulmonary veins in patients with atrial fibrillation", Am J Cardiology, 91:159-63 (2003).

Dennis, et al., "Protein glycosylation in development and disease", BioEssays, 21: 412-421 (1999).

Deschamps, et al., "Pathways of matrix metalloproteinase induction in heart failure: Bioactive molecules and transcriptional regulation", Cardiovasc Res, 69:666-76 (2006).

Devereux, et al., Echocardiographic assessment of left ventricular hypertrophy: Am. J. Cardiol. 57: 450 (1986).

Diez, et al., "Losartandependent regression of myocardial fibrosis is associated with reduction of left ventricular chamber stiffness in hypertensive patients", Circulation, 105:2512-17 (2002).

Dispersyn, et al., "Cardiomyocyte remodelling during myocardial hibernation and atrial fibrillation: prelude to apoptosis", Cardiovasc Res, 43:947-57 (1999).

Divakaran and Mann, "The Emerging Role of MicroRNAs in Cardiac Remodeling and Heart Failure", Circ Res., 103:1072-83 (2008).

Dong, et al., "MicroRNA Expression Signature and the Role of MicroRNA-21 in the Early Phase of Acute Myocardial Infarction", J Biol Chem., 284(43):29514-25 (2009).

Douglas, et al., "Computational sequence analysis of the tissue inhibitor of metalloproteinase family", J. Protein Chem, 16:237-55 (1997).

Ducharme, et al., "Targeted deletion of matrix metalloproteinase-9 attenuates left ventricular enlargement and collagen accumulation after experimental myocardial infarction", J Clin Invest, 106:55-62 (2000).

Duisters, et al., "miR-133 and miR-30 Regulate Connective Tissue Growth Factor. Implications for a Role of MicroRNAs in Myocardial Matrix Remodeling", Circ Res, 104:170-8 (2009).

Edwards, et al., "The roles of tissue inhibitors of metalloproteinases in tissue remodeling and cell growth", Intl. J Obes Metab Disord., 20;S9-S15 (1996).

Elia, et al., "The knockout of miR-143 and -145 alters smooth muscle cell maintenance and vascular homeostasis in mice: correlates with human disease", Cell Death Differ., 16(12):1590-98 (2009).

Erlebacher, et al., "Early dilation of the Infarcted segment in acute transmural myocardial infarction: role of infarct expansion in acute left ventricular enlargement", J Am Coil Cardiol, 4(2)201-8 (1984).

Esteve, et al., "Protein kinase C-zeta regulates transcription of the matrix metalloproteinase-9 gene induced by IL-i and TNF-alpha in glioma cells via NF-kappa B", J Biol Chem, 277(38):35150-5 (2002).

Etoh, et al., "Myocardial and interstitial matrix metalloproteinase activity after acute myocardial infarction in pigs", Am J Physiol Heart Circ Physiol, 281:H987-H994 (2001).

Falcone, et al., "Plasma Levels of Soluble Receptor for Advanced Glycation End Products and Coronary Artery Disease in Nondiabetic Men", Arterioscler Thromb Vasc Biol, 25:1032-7 (2005).

Felkin, et al., "A quantitative gene expression profile of matrix metalloproteinases (MMPS) and their inhibitors (TIMPS) in the myocardium of patients with deteriorating heart failure requiring left ventricular assist device support", J Heart Lung Transpl., 26:1413-19 (2006).

Fini, et al., "Regulation of matrix metalloproteinase gene expression", Matrix Metalloproteinases. San Diego: Academic, 299-356, (1998).

Fragakis, et al., "Reversion and maintenance of sinus rhythm in patients with permanent atrial fibrillation by internal cardioversion followed by biatrial pacing", Pacing Clin Electrophysiol 25:278-86 (2002).

Frick, et al., "Factors predicting success rate and recurrence of atrial fibrillation after first electrical cardioversion in patients with persistent atrial fibrillation", Clin Cardiol , 24:238-44 (2001).

Friedman, et al., "Most mammalian mRNAs are conserved targets of microRNAs", Genome Res. 19(1):92-105 (2009).

Frustaci, et al., "Histological Substrate of Atrial Biopsies in Patients With Lone Atrial Fibrillation", Circulation, 96:1180-4 (1997).

Galis and Khatri, "Matrix metalloproteinases in vascular remodeling and atherogenesis: the good, the bad and the ugly", Circ Res., 90: 251-62 (2002).

Goette, et al., "Calpains and cytokines in fibrillating human atria", Am J Physiol Heart Circ Physiol , 283:H264-H272 (2002).

Goffin, et al., "Expression pattern of metalloproteinases and tissue inhibitor of matrix metalloproteinases in cycling human endometrium", Biol Reprod, 69:976-84 (2003).

Goldberg, et al., "Human 72-kilodalton type IV collagenase forms a complex with a tissue inhibitor of metalloproteinase designated TIMP", PNAS, 86:8207-11 (1989).

Gomez, et al., "Tissue inhibitor of metalloproteinases: structure, regulation, and biological functions", EJCB, 74:111-12 (1997).

(56) References Cited

OTHER PUBLICATIONS

Greene, et al., "Molecular cloning and characterization of human tissue inhibitor of metalloproteinase 4", J Biol Chem 271(48):30375-80 (1996).
Grimson, et al., "MicroRNA targeting specificity in mammals: determinants beyond seed pairing", Mol Cell., 27(1):91-105 (2007).
Grishok, et al., "Genes and mechanisms related to RNA interference regulate expression of the small temporal RNAs that control C. elegans developmental timing", Cell, 106(1):23-34 (2001).
Gross, et al., "Collagenolytic activity in amphibian tissues: a tissue culture assay", PNAS,48:1014-22 (1962).
Gunasinghe, et al., "Contributory role of matrix metalloproteinases in cardiovascular remodeling", Cardiovasc & Haemato Disorders, 1(2):75-91(1996).
Gunja-Smith, et al., "Remodeling of human myocardial collagen in idiopathic dilated cardiomyopathy: role of metalloproteinases and pyridinoline cross links", Am J Path, 148:1639-48 (1996).
Haro, et al., "Matrix metalloproteinase-7 dependent release of tumor necrosis factor alpha in a model of herniated disc resorption", J Clin Invest 105:143-50 (2000).
Herman, et al., "Expression of neutrophil collagenase (matrix metalloproteinase-8) in human atheroma: a novel collagenolytic pathway suggested by transcriptional profiling", Circulation 104;(2001), 1899-1904.
Heymans, et al., "Inhibition of plaminogen activators or matrix metalloproteinases prevents cardiac rupture but impairs therapeutic angiogenesis and causes cardiac failure", Nature Med 5:1135-42 (1999).
Hirohata, et al., "Time dependent alterations of serum matrix metalloproteinase-1 and metalloproteinase-1 and metalloproteinase-1 tissue inhibitor after successful reperfusion of acute myocardial infarction", Heart, 78:278-84 (1997).
Hobbs, et al., "Reversal of atrial electrical remodeling after cardioversion of persistent atrial fibrillation in humans", Circulation, 101:1145-51 (2000).
Hofmann, et al., "RAGE mediates a novel proinflammatory axis: a central cell surface receptor for S100/calgranulin polypeptides", Cell, 97:889-901(1999).
Hojo, et al., "Expression of matrix metalloproteinases in patients with acute myocardial infarction", Jpn Circ J, 65; 71-75 (2001).
Holmbeck, et al., "MT1-MMP: a tethered collagenase", J Cell Physiol, 200:11-9 (2004).
Hunt, et al., "The amino-terminal portion of pro-brain natriuretic peptide (Pro-BNP) circulates in human plasma", Biochem Biophys Res Commun. 214:1175-83 (1995).
Ikonomidis, et al., "Effects of deletion of the matrix metalloproteinase 9 gene on development of murine thoracic aortic aneurysms", Circulation, 112(9 Suppl):I242-8 (2005).
Ikonomidis, et al., "Expression of matrix metalloproteinases and endogenous inhibitors within ascending aortic aneurysms of patients with bicuspid or tricuspid aortic valves", J Thorac Cardiovasc Surg. 133(4)1028-36 (2007).
Ikonomidis, et al., "Expression of matrix metalloproteinases and endogenous inhibitors within ascending aortic aneurysms of patients with Marfan syndrome", Circulation., 114(1 Suppl):I365-70 (2006).
Inokubo, et al., "Plasma levels of matrix metalloproteinase-9 and tissue inhibitor of metalloproteinase-1 are increased in the coronary circulation in patients with acute coronary syndrome", Am Heart J, 141:211-7 (2001).
Isselbacher, "Thoracic and abdominal aortic aneurysms", Curr., 111(6):816-28 (2005).
Joffs, et al., "Cardiopulmonary bypass induces the synthesis and release of matrix metalloproteinases", Ann Thorac Surg., 71:1518-23 (2001).
Jones, et al., "Alterations in membrane type-1 matrix metalloproteinase abundance after the induction of thoracic aortic aneurysm in a murine model", Am J Physiol Heart Circ Physiol. 299(1):H114-24 (2010).

Jones, et al., "Selective microRNA suppression in human thoracic aneurysms: relationship of miR-29a to aortic size and proteolytic induction", Circ Cardiovasc Genet, 4(6):605-13 (2011), Abstract Only.
Jones, et al., "Spatiotemporal expression and localization of matrix metalloproteinase-9 in a murine model of thoracic aortic aneurysm", J Vasc Surg., 44(6):1314-21(2006).
Kaden, et al., "Time dependent changes in the plasma concentration of matrix metalloproteinase 9 after acute myocardial infarction", Cardiology, 99:140-4 (2003).
Kai, et al., "Peripheral blood levels of matrix metalloproteases-2 and -9 are elevated in patients with acute coronary syndromes", J Am Coll Cardiol, 32:368-72 (1998).
Kenchaiah and Pfeffer, "Cardiac remodeling in systemic hypertension", Med Clin N Am., 88:115-30 (2004).
Kostin, et al., "Structural correlate of atrial fibrillation in human patients", Cardiovas.Res., 54:361-79 (2002).
Kozomara, et al., "miRBase: integrating microRNA annotation and deep-sequencing data", Nucleic Acids Res., 39(Database issue):D152-157 (2011).
Laemmli, "Cleavage of structural proteins during the assembly of the head of bacteriophage T4", Nature, 227:680-5 (1970).
Lagos-Quintana, et al., "Identification of novel genes coding for small expressed RNAs", Science, 294(5543):853-8 (2001).
Lakatta and Levy, "Arterial and cardiac aging: major shareholders in cardiovascular disease enterprises: Pt I: aging arteries: a "set up" for vascular disease", Circulation,107(1):139-46 (2003).
Lau, et al., "An abundant class of tiny RNAs, with probable regulatory roles in Caenorhabditis elegans", Science, 294(5543):858-62 (2001).
Laviades, et al., "Abnormalities of the extracellular degradation of collagen type I in essential hypertension", Circulation., 98(6):535-40 (1998).
Lee and Ambros, "An extensive class of small RNAs in Caenorhabditis elegans", Science, 294(5543):862-4 (2001).
Lellouche, et al., "Usefulness of plasma B-type natriuretic peptide in predicting recurrence of atrial fibrillation one year after external cardioversion", Am J Cardiol,95:1380-82 (2005).
Lemaire, et al., "Matrix metalloproteinases in ascending aortic aneurysms: bicuspid versus trileaflet aortic valves", J Surg Res,123(1):40-8 (2005).
Levy, et al., "The progression from hypertension to congestive heart failure" . JAMA, 275:1557-62 (1996).
Lewis, et al., "Conserved seed pairing, often flanked by adenosines, indicates that thousands of human genes are microRNA targets", Cell., 120(1)15-20 (2005).
Li, et al., "Attenuation of micro-RNA-1 derepresses the cytoskeleton regulatory protein twinfilin-1 to provoke cardiac hypertrophy", J Cell Sci., 123(pt14):2444-52 (2010).
Li, et al., "Differential expression of tissue inhibitors of metalloproteinases in the failing human heart", Circ., 98;1728-34 (1998).
Li, et al., "Downregulation of matrix metalloproteinases and reduction in collagen damage in the failing human heart after support with left ventricular assist devices", Circ,104:1147-52 (2001b).
Li, et al., "Matrilysin shedding of syndecan-1 regulates chemokine mobilization and transepithelial efflux of neutrophils in acture lung injury", Cell ,111:635-46 (2002).
Li, et al., MMP/TMP expression in spontaneously hypertensive heart failure rats: the effect of ACE and MMP-inhibition, Cardio Res, 46:298-306 (2000).
Li, et al., "Proinflammatory cytokines regulate tissue inhibitors of metalloproteinases and disintegrin metalloproteinase in cardiac cells", Cardiovasc Res., 42(1):162-72 (1999).
Li, et al., "Real-Time Polymerase Chain Reaction MicroRNA Detection Based on Enzymatic Stem-Loop Probes Ligation", Anal Chem., 1:81(13):5446-51 (2009).
Li-Saw-Hee, et al., "Lip GYH: Matrix metalloproteinase-9 and tissue inhibitor metalloproteinase-1 levels in essential hypertension. Relationship to left ventricular mass and anti-hypertensive therapy", Int J Cardiol. 75:43-7 (2000).
Li and Wong, "Model-based analysis of oligonucleotide arrays: expression index computation and outlier detection", PNAS, 98(1):31-6 (2001a).

(56) References Cited

OTHER PUBLICATIONS

Liao, et al., "A microRNA profile comparison between thoracic aortic dissection and normal thoracic aorta indicates the potential role of microRNAs in contributing to thoracic aortic dissection pathogenesis", J Vasc Surg., 53(5):1341-9.e3 (2011).
Liao, et al.,"Cardiotrophin-1 (CT-1) can protect the adult heart from injury when added both prior to ischaemia and at reperfusion", Cardiovasc. Res., 53:902-10 (2002).
Lin, et al., "Predictors of clinical recurrence after successful electrical cardioversion of chronic persistent atrial fibrillation: clinical and electrophysiological observations", Cardiol., 97:133-7 (2002).
Lindsay, et al., "TIMP-1. A marker of left ventricular diastolic dysfunction and fibrosis in hypertenstion", Hypertension, 40:136-41 (2002).
Lindsey, et al., "Extracellular matrix remodeling following myocardial injury", Ann Med., 35:316-26 (2003).
Liu, et al., "Identification and characteristics of microRNAs with altered expression patterns in a rat model of abdominal aortic aneurysms", Tohoku J Exp Med., 222(3):187-93 (2010).
Liu, et al., "microRNA-133a regulates cardiomyocyte proliferation and suppresses smooth muscle gene expression in the heart", Genes Dev., 22(23):3242-54 (2008).
Liu, et al., "Preparation and characterization of recombinant tissue inhibitor of metaloproteinase 4", Am Soc Biochem Mol Biol, , 272:20479-83 (1997).
Liu, et al., "Renal medullary microRNAs in Dahl salt-sensitive rats: miR-29b regulates several collagens and related genes", Hypertension, 55(4):974-82 (2010b).
Lloyd-Jones,et al., "Lifetime risk for developing congestive heart failure:The Framingham Study", Circ., 06:3068-72 (2002).
Longo, et al., "Matrix metalloproteinases 2 and 9 work in concert to produce aortic aneurysms", J Clin Invest. 110(5):625-32 (2002).
Lopez, et al., "Biochemical assessment of myocardial fibrosis in hypertensive heart disease", Hypertension, 38:1222-26 (2001b).
Lopez, et al., "Usefulness of serum carboxy-terminal propeptide of procollagen type I in assessment of the cardioreparative ability in antihypertensive treatment in hypertensive patients",Circ, 104:286-91 (2001a).
Mair, et al., "The impact of cardiac natriuretic peptide determination on the diagnosis and management of heart failure", Clin Chem Lab Med., 39:571-88 (2001).
Marin, et al., "Is Thrombogenesis in Atrial Fibrillation Related to Matrix Metalloproteinase-1 and Its Inhibitor, TIMP-1", Stroke,34:1181-6 (2003).
Maron, et al.,"Hypertrophic cardiomyopathy: a systematic review", JAMA, 287:1308-20 (2002).
Matrisian, "Metalloproteinases and their inhibitors in matrix remodeling", Trends in Genetics, 6:121-5 (1990), Abstract Only.
Matsudaira,et al., "SDS microslab linear gradient polyacrylamide gel electrophoresis", Anal Biochem, 87:386-96 (1987).
McMillan, et al., "In situ localization and quantification of mRNA for 92-kD type IV collagenase and its inhibitor in aneurysmal, occlusive, and normal aorta", Arterioscler Thromb Vasc Biol. 15(8):1139-44 (1995a).
McMillan, et al., "In situ localization and quantification of seventy-two-kilodalton type IV collagenase in aneurysmal, occlusive, and normal aorta", J Vasc Surg, 22(3):295-305 (1995b).
Mitchell, et al., "Circulating microRNAs as stable blood-based markers for cancer detection", PNAS, 105(30):10513-8 (2008).
Montaner, et al., "Matrix Metalloproteinase Expression Is Related to Hemorrhagic Transformation After Cardioembolic Stroke", Stroke, 32:2762-7 (2001b).
Montaner, et al., "Matrix metalloproteinase-9 pretreatment level predicts intracranial hemorrhagic complications after thrombolysis in human stroke", Circ, 107:598-603 (2003).
Montaner , et al.. "Matrix Metalloproteinase Expression After Human Cardioembolic Stroke: Temporal Profile and Relation to Neurological Impairment", Stroke, 32:1759-66 (2001).
Moon, et al., "ERK1/2 mediates TNF-alpha induced matrix metalloproteinase-9 expression in human vasuclar smooth muscle cells via the regulation of NF-kappaB and AP-1: Involvement of the ras dependent pathway", J Cell Physiol., 198:417-27 (2004).
Mukherjee, et al., "Myocardial infarct expansion and matrix metalloproteinase inhibition", Circulation, 107(4):618-25 (2003).
Nagase, "Activational mechansims of matrix metalloprteinases", Biol Chem., 378:151-60 (1997).
Nagueh, et al., "Changes in left ventricular diastolic function 6 months after nonsurgical septal reduction therapy for hypertrophic obstructive cardiomyopathy", Circ., 93:344-7 (1999a).
Nagueh, et al., "Changes in left ventricular filling and left atrial function six months after nonsurgical septal reduction therapy for hypertrophic obstructive cardiomyopathy", J Am Coil Cardiol, 34;1123-8 (1999b).
Nagueh, et al., "Decreased expression of tumor necrosis factor-alpha and regression of hypertrophy after nonsurgical septal reduction therapy for patients with hypertrophic obstructive cardiomyopathy", Circ., 103(14):1844-50 (2001).
Nagueh, et al., "Doppler estimation of left ventricular filling pressure in sinus tachycardia. A new application of tissue Doppler imaging", Circ., 98:1644-50 (1998).
Neuhoff, et al., "Clear background and highly sensitive protein staining with Coomassie Blue dyes in polyacrylamide gels: A systematic analysis", Electrophoresis, 6:427-48 (1985).
Neuhoff, et al., "Improved staining of proteins in polyacrylamide gels including isoelectric focusing gels with clear background at nanogram sensitivity using Coomassie Brilliant Blue G-250 and R-250", Electrophoresis, 9:255-262 (1988).
O'Farrell, "High Resolution Two-dimensional Electrophoresis of Proteins", J Biol Chem, 250:4007-21 (1975).
Ornstein, "Disc electrophoresis—I: Background and theory", Ann. NY Acad. Sci., 121:321-49 (1964).
Parsons, et al., "Matrix metalloproteinases", Brit J Surg, 84:160-6 (1997).
Peterson, et al., "Evolution of matrix metalloproteinase and tissue inhibitor expression during heart failure progression in the infracted rat", Cardiovas Res, 46:307-15 (2000).
Peterson, et al., "Matrix metalloproteinase inhibition attenuates left ventricular remodeling and dysfunction in a rat model of progressive heart failure", Circ,103(18): 2303-9 (2001).
Pfeffer, et al., "Ventricular remodeling after myocardial infarction. Experimental observations and clinical implications", Circ., 81:1161-72 (1990).
Pozzoli, et al., "Predictors of primary atrial fibrillation and concomitant clinical and hemodynamic changes in patients with chronic heart failure: a prospective study in 344 patients with baseline sinus rhythm", J Am Coll Cardiol., 32:197-204 (1998).
Psaty, et al., "Incidence of and risk factors for atrial fibrillation in older adults", Circ., 96:2455-61 (1997).
Qin and Zhang, "MicroRNAs in vascular disease", J Cardiovasc Pharmacol., 57(1):8-12 (2011).
Radomski, et al.,"Identification, regulation and role of tissue of tissue inhibitor of metalloproteinases-4 (TIMP-4) in human platelets", Br J Pharmaco 137(8).(2002), 1330-1338.
Rohde, et al., "Matrix metalloproteinase inhibition attenuates early left ventricular enlargement after experimental myocardial infarction in mice", Circ, 99:3063-70 (1999).
Roy, et al., "MicroRNA expression in response to murine myocardial infarction: miR-21 regulates fibroblast metalloprotease-2 via phosphatase and tensin homologue", Cardiovasc Res., 82(1):21-9 (2009).
Sahn, et al., "Recommendations regarding quantitation in M-mode echocardiography:results of a survey of echocardiographic measurements", Circ., 58:1072-83 (1978).
Sanfilippo, et al., "Atrial enlargement as a consequence of atrial fibrillation. A prospective echocardiographic study", Circ., 82:792-7 (1990).
Sawicki, et al., "Release of gelatinase A during platelet activation mediates aggregation", Nature, 386:616-9 (1997).
Schillaci, et al., "Prognostic significance of left ventricular diastolic dysfunction in essential hypertension", J Am Coil Cardiol., 39:2005-11 (2002).
Schiller, et al., "Recommendations for quantitation of the left ventricle by two-dimensional echocardiography. American Society of

(56) References Cited

OTHER PUBLICATIONS

Echocardiography Committee on Standards, Subcommittee on Quantitation of Two-Dimensional Echocardiograms.", J Am Soc Enchocaridiogr., 2(5): 358-67 (1989).
Schleicher, et al., "Increased accumulation of the glycoxidation product N (epsilon)-(carboxymethyl)lysine in human tissues in diabetes and aging", J. Clin. Invest., 99(3):457-68 (1997).
Schotten, et al., "Cellular mechanisms of depressed atrial contractility in patients with chronic atrial fibrillation", Circ., 103: 691-8 (2001).
Schotten, et al., "Electrical and contractile remodeling during the first days of atrial fibrillation go hand in hand", Circ., 107:1433-9 (2003).
Schulz-Menger, et al., "The value of magnetic resonance imaging of the left ventricular outflow tract in patients with hyupertrophic obstructive cardiomyopahty after septal artery embolization", Circ., 101:1764-6 (2000).
Schulze, et al., "Imbalance between tissue inhibitor of metalloproteinase-4 and matrix metalloproeinases during acute myocardial ischemic-reperfusion injury", Circ, 107:2487-92 (2003).
Schwartz, et al., "Impact of pre-existing conditions, age and the length of cardiopulmonary bypass on postoperative outcome after repair of the ascending aorta and aortic arch for aortic aneurysms and dissections", Interact Cardiovasc. Thorac Sug., 7(5):850-4 (2008).
Schwartzkopff, et al., "Elevated serum markers of collagen degradation in patients with mid to moderate dilated cardiomyopathy", Eur. J Heart Fail., 4:439-44 (2002).
Sen, et al., "Micromanaging vascular biology: tiny microRNAs play big band", J Vasc Res., 46(6):527-40 (2009).
Sharp, et al., "Serum levels of low molecular weight advanced glycation end products in diabetic subjects", Diabet Med, 20(7): 575-9 (2003).
Sheng, et al., "Cardiotrophin-1 displays early expression in the murine heart tube and promotes cardiac myocyte survival", Development, 122:419-28 (1996).
Shirwany, et al., "Extracellular matrix remodeling in hypertensive heart disease", J of Am College of Cardiology, 48:97-98 (2006).
Sinha, et al., "A biologic basis for asymmetric growth in descending thoracic aortic aneurysms: a role for matrix metalloproteinase 9 and 2", J Vasc Surg., 43(2):342-8 (2006).
Siwik, et al., "Oxidative stress regulates collagen synthesis and matrix metalloproteinase activity in cardiac fibroblasts", Am J Phys., 280:C53-60 (2001).
Small, et al., "MicroRNAs Add a New Dimension to Cardiovascular Disease", Circ., 121:1022-32 (2010).
Spencer, et al., "Alcohol septal ablation in hypertrophic obstructive cardiomyopathy: the need for registry", Circ., 102;600-01 (2000).
Spinale, et al., "A matrix metalloproteinase induction/activation system exists in the human myocardium and is upregulated in heart failure", Circ., 102;1944-9 (2000).
Spinale, et al., "Extracellular degradative pathways in myocardial remodeling and progression to heart failure", J Cardiac Failure, 8:S332-8 (2002).
Spinale, et al., "Matrix metalloporeinase inhibition during developing congestive heart failure in pigs: effects on left ventricular geometry and function", Circ Res, 85:364-76 (1999).
Spinale, et al., "Time-dependent changes in matrix metalloproteinase activity and expression during the progression of congestive heart failure: relation to ventricular and myocyte function", Circ. Res., 82(4):482-95 (1998).
Spinale, "Chronic matrix metalloproteinase inhibition following myocardial infarction in mice: Differential effects on short and long-term survival", J Pharmacol. Exp. Ther., 318(3):966-73 (2006).
Spinale, "Matrix metalloproteinases. Regulation and dysregulation in the failing heart", Circ. Res., 90:520-30 (2002).
St. John Sutton, et al., "Quantitative two-dimensional echocardiographic measurements are major predictors of adverse cardiovascular events after myocardial infarction. The protective effects of captopril", Circ., 89;68-75 (1994).
Steele, et al., "MBP-1 upregulates miR-29b that represses Mcl-1, collagens, and matrix-metalloproteinase-2 in prostate cancer cells", Genes Cancer, 1(4):381-7 (2010).
Steinberg, et al., "Rapid and simple single nanogram detection of glycoproteins in polyacrylamide gels on electroblots", Proteomics, 1(7): 841-55 (2000).
Stroud, et al., "Plasma monitoring of the myocardial specific tissue inhibitor of metalloproteinase-4 after alcohol septal ablation in hypertrophic obstructive cardiomyopathy", J Card Fail, 11:124-30 (2005).
Sundstrom, et al., "Relations of plasma matrix metalloproteinase-9 to clinical cardiovascular risk factors and echocardiographic left ventricular measures: the Framingham Heart Study", Circulation, 109:2850-56 (2004).
Tamarina, et al., "Expression of matrix metalloproteinases and their inhibitors in aneurysms and normal aorta", Surgery, 122(2):264-71; discussion 271-262 (1997).
Tayebjee, et al., "Matrix metalloproteinase-9 and tissue inhibitor of metalloproteinase-1 in hypertension and their relationship to cardiovascular risk and treatment: a substudy of the Anglo-Scandinavian Cardiac Outcomes Trial (ASCOT)", Am J Hypertens.,17:764-9 (2004).
Tayebjee, et al, "Tissue inhibitor of metalloproteinase-1 and matrix metalloproteinase-9 levels in patients with hypertension Relationship to tissue Doppler indices of diastolic relaxation", Am J Hypertens., 17:770-4 (2004).
Tayebjee, et al., "Tissue inhibitor of metalloproteinse-1 is a marker of diastolic dysfunction using tissue doppler in patients with type 2 diabetes and hypertension", Eur J Clin Invest.35:8-12 (2005).
Thijssen, et al., "Structural remodelling during chronic atrial fibrillation: act of programmed cell survival", Cardiovas Res, 52:14-24 (2001).
Thomas, et al., "Increased matrix metalloproteinase activity and selective upregulation inLV myocardium from patients with end-stage dilated cardiomyopathy", Circ, 97:1708-15 (1998).
Timms, et al., "Plasma tissue inhibitor of metalloproteinase-1 levels are elevated in essential hypertension and related to left ventricular hypertrophy", Am J Hyper,15:269-72 (2002).
Todd, et al., "Prevalence and significance of focal sources of atrial arrhythmia in patients undergoing cardioversion of persistent atrial fibrillation", J Cardiovasc Electrophysiol., 11:616-22 (2000).
Tsuruda, et al., "Matrix metalloproteinases: pathways of induction by bioactive molecules", Heart Fail Rev., 9:53-61 (2004).
Tziakes, et al., "N-terminal pro-B-type natriuretic peptide and matrix metalloproteinases in early an dlate left ventricular remodeling after acute myocardial infarction", Am J Cardio., 96:31-4 (2005).
U.S. Appl. No. 12/307,985 Prosecution history, filed 2009.
U.S. Appl. No. 12/299,999 Prosecution history, filed 2009.
Van Gelder, et al., "Prediction of uneventful cardioversion and maintenance of sinus rhythm from direct-current electrical cardioversion of chronic atrial fibrillation and flutter", Am J Cardiol. 68:41-6 (1991).
van Rooij, et al. "Dysregulation of microRNAs after myocardial infarction reveals a role of miR-29 in cardiac fibrosis", PNAS, 105(35):13027-32 (2008).
Vincenti, "The matrix metalloproteinase (MMP) and tissue inhibitor of metalloproteinase (TIMP) genes. Transcriptional and post-transcriptional regulation, signal transduction and cell-type-specific expression", Methods Mol Biol., 151:121-48 (2001).
Visse, et al., "Matrix metalloproteinases and tissue inhibitors of metalloproteinases: structure, function, and biochemistry", Circ Res., 92:827-39 (2003).
Voller, et al., "Enzyme immunoassays with special reference to ELISA techniques", J Clin. Pathol., 31:507-20 (1978).
Vu and Werb, "Matrix metalloproteinases: effectors of development and normal physiology", Genes Dev., 14:2123-33 (2000).
Wachtell, et al., "Left ventricular filling patterns in patients with systemic hypertension and left ventricular hypertrophy (The Life Study)", Am J Cardiol., 85:466-72 (2000).
Wassef, et al., "Pathogenesis of abdominal aortic aneurysms: a multidisciplinary research program supported by the National Heart, Lung, and Blood Institute", J Vas Surg, 34:730-8 (2001).

(56) References Cited

OTHER PUBLICATIONS

Wautier, et al., "Receptor-mediated endothelial cell dysfunction in diabetic vasculopathy. Soluble receptor for advanced glycatlon end products blocks hyperpermeability in diabetic rats", J. Clin. Invest. 97:238-43 (1996).

Wazni, et al., "C reactive protein concentration and recurrence of atrial fibrillation after electrical cardioversion", Heart, 91:1303-5 (2005).

Webb, et al., "Specific temporal profile of matrix metalloproteinase release occurs in patients after myocardial infarction: relation to left ventricular remodeling", Circulation, 114(10):1020-27 (2006).

Weber, et al., "Pathological hypertrophy and cardiac interstitium: Fibrosis and renin-angiotensin-aldosterone system", Circ., 83:1849-65 (1991).

Weber, et al., "Structural remodeling in hypertensive heart disease and the role of hormones", Hypertension, 23:869-77 (1994).

White, et al., "Left ventricular end-systolic volume as the major determinant of survival after recovery from myocardial infarction", Circ., 76(1):44-51 (1987).

Wilson, et al., "Plasma matrix metalloproteinase and inhibitor profiles in patients with heart failure", J Card Fail., 8:390-98 (2002).

Wilson, et al., "Region and type-specific induction of matrix metalloproteinases occurs with post-myocardial infarction remodeling", Circ., 107(22):2857-63 (2003).

Woessner, et al., "Activation of the zymogen forms of MMPs", Matrix metalloproteinase and TIMPs. Oxford Univerity Press, Oxford UK, pp. 72-86 (2000).

Woessner, et al., "The matrix metalloproteinase family", Matrix metalloproteinases. Parks WC, Mecham RP, eds. Academic Press, San Diego. Ppl-14 (1998).

Wyse, et al., "A Comparison of Rate Control and Rhythm Control in Patients with Atrial Fibrillation", N Engl J Med ., 347:1825-33 (2002).

Xu, et al., "The *Drosophila* microRNA Mir-14 suppresses cell death and is required for normal fat metabolism", Curr. Biol., 13(9):790-5 (2003).

Yang, et al., "Advances in diastolic heart failure", World J Cardiol., 2(3):58-63 (2010).

Yarbrough, et al., "Selective targeting and timing of matrix metalloproteinase inhibition in post-myocardial infarction remodeling", Circ., 108:1753-59 (2003).

Yasmin, et al., "Matrix metalloproteinase-9 (MMP-9), MMP-2, and serum elastase activity are associated with systolic hypertension and arterial stiffness", Arterioscler Thromb Vasc Biol., 25 (2):372 (2005).

Yu, et al., "Reversal of atrial electrical remodeling following cardioversion of long-standing atrial fibrillation in man", Cardiovas. Res., 42:470-6 (1999).

Zervoudaki, et al., "Plasma levels of active extracellular matrix metalloproteinases 2 and 9 in patients with essential hypertension before and after antihypertensive treatment", J Hum Hypertens.,17:119-24 (2003).

Zhong, et al., "Changes in metalloproteinase and tissue inhibitor of metalloproteinase during tachycardia-induced cardiomyopathy by rapid atrial pacing in dogs", Cardiology, 106:22-8 (2006).

Zile and Brutsaert, "New concepts in diastolic dysfunction and diastolic heart failure. Part II: Causal mechanisms and treatment", Circ., 105:1503-8 (2002a).

Zile and Brutsaert, "New concepts in diastolic dysfunction and diastolic heart failure. Part I: Diagnosis, prognosis, measurements of diastolic function", Circ.,105:1387-93 (2002b).

U.S. Appl. No. 12/522,238 Prosecution history, filed 2010.

\* cited by examiner

| | LVH | DHF |
|---|---|---|
| miR-1 | 2.0±0.4* | 1.6±0.6 |
| miR-21 | 4.7±0.8* | 3.1±0.8 |
| miR-29a | 2.3±0.5* | 1.3±0.4 |
| miR-133a | 1.9±0.4* | 1.3±0.4 |
| miR-760 | 2.1±0.3* | 1.1±0.2 |

*=p<0.05 vs. Control.

| | Absolute Baseline Values (x10⁻⁶) | | Change Following I/R (%) | |
|---|---|---|---|---|
| miRs | INTf | Plasma | INTf | Plasma |
| miR-1 | 0.20±0.06 | 0.06±0.02* | 54±17* | 290±130 |
| miR-21 | 1.37±0.25 | 28.70±8.73* | 101±10 | 35±15+ |
| miR29a | 1.45±0.37 | 7.14±2.48* | 61±11* | 49±14+ |
| miR-133a | 1.23±0.42 | 0.31±0.11* | 70±40 | 712±184+ |
| miR-486 | 0.10±0.03 | 228.16±87.38* | 117±41 | 162±56 |
| miR-760 | 4.78±2.15 | 0.76±0.27* | 65±16* | 146±28 |

MEAN±SEM ; * p < 0.05 vs. Baseline INTf; +p < 0.05 vs. Respective Baseline

A

B

ASSESSING LEFT VENTRICULAR REMODELING VIA TEMPORAL DETECTION AND MEASUREMENT OF MICRORNA IN BODY FLUIDS

CROSS-REFERENCE TO RELATED APPLICATIONS

This application claims benefit of U.S. Provisional Application No. 61/261,774, filed Nov. 17, 2009. Application No. 61/261,774, filed Nov. 17, 2009, is hereby incorporated herein by reference in its entirety.

FIELD OF THE INVENTION

The disclosed invention is generally in the field of cardiac failure and specifically in the area of diagnosis, prognosis, and monitoring of cardiac failure.

BACKGROUND OF THE INVENTION

MicroRNAs (miRNAs) are noncoding RNAs that bind to target mRNAs and reduce their expression through translational repression or mRNA degradation. Measurements made in myocardial tissue have suggested the miRNAs play a regulatory role in myocardial growth, fibrosis, and remodeling.

MicroRNAs have been isolated from C. elegans, Drosophila, and humans (Lagos-Quintana et al., 2001; Lau et al., 2001; Lee and Ambros, 2001). Several hundred miRNAs have been identified in plants and animals—including humans—which do not appear to have endogenous siRNAs. Thus, while similar to siRNAs, miRNAs are nonetheless distinct. miRNAs thus far observed are approximately 21-22 nucleotides in length and they arise from longer precursors, which are transcribed from non-protein-encoding genes. See review of Carrington et al. (2003). The precursors form structures that fold back on each other in self-complementary regions; they are then processed by the nuclease Dicer in animals or DCL1 in plants. miRNA molecules interrupt translation through imprecise base-pairing with their targets.

Most miRNAs are involved in gene regulation. Some of these miRNAs, including lin-4 and let-7, inhibit protein synthesis by binding to partially complementary 3' untranslated regions (3' UTRs) of target mRNAs. Others, including the Scarecrow miRNA found in plants, function like siRNA and bind to perfectly complementary mRNA sequences to destroy the target transcript (Grishok et al., 2001). Some miRNAs, such as lin-4, let-7, mir-14, mir-23, and bantam, have been shown to play critical roles in cell differentiation and tissue development (Ambros, 2003; Xu et al., 2003). Others are believed to have similarly important roles because of their differential spatial and temporal expression patterns.

BRIEF SUMMARY OF THE INVENTION

Disclosed are methods and materials for assessing cardiac failure, cardiac hypertrophy, and left ventricular remodeling using microRNA levels. The level of microRNAs can be measured in a body fluid, such as plasma and serum. Disclosed is method comprising detecting one or more target microRNAs in a body fluid of a subject at a plurality of different times. The temporal pattern of the level of the one or more target microRNAs can indicates the presence, severity, or a combination of left ventricular remodeling in the subject.

The presence, severity, or a combination of left ventricular remodeling in the subject can be indicated by comparing the temporal pattern of the level of the one or more target microRNAs to one or more reference temporal patterns. The one or more microRNAs can comprise one or more of miR-1, miR-21, miR-23a, miR-29a, miR-30, miR-133a, miR-150, miR-195, miR-199, miR-208, miR-214, and miR-125b. The one or more microRNAs can comprise one or more of miR-1, miR-21, miR-29a, miR-133a, miR-208, and miR-125b. The one or more microRNAs can comprise one or more of miR-1, miR-21, miR-29a, miR-133a, and miR-208.

The body fluid can be, for example, blood, plasma, serum, or lymphatic fluid. The plurality of different times at which the one or more microRNAs are detected can comprise two or more times separated by 1, 2, 3, 4, 5, 10, 15, 20, 23, 24, 25, 26, 27, 28, 30, 35, 40, 45, 50, 55, 60, 62, 65, 70, 75, 80, 85, 86, 87, 88, 89, and 90 days. The plurality of different times at which the one or more microRNAs are detected can comprise two or more times separated by 2, 3, 23, and 62 days. The level of the one or more target microRNAs can comprise the measured level of the one or more target microRNAs normalized to the measured level of a reference RNA in the body fluid. The reference RNA can be snRNA U6.

The level of the one or more target microRNAs can comprise the measured level of the one or more target microRNAs expressed as the fold difference of the measured level of the one or more target microRNAs to the measured level of the one or more target microRNAs in a reference subject. The level of the one or more target microRNAs can comprise the measured level of the one or more target microRNAs normalized to the measured level of a reference RNA in the body fluid expressed as the fold difference of the normalized level of the one or more target microRNAs to the measured level of the one or more target microRNAs in the same body fluid of reference subject normalized to the measured level of a reference RNA in the body fluid of the reference subject.

The level of the one or more target microRNAs in a reference subject can be measured at the same time as the level of the one or more target microRNAs is measured in the subject. The level of the one or more target microRNAs in a reference subject can be measured at a different time than the level of the one or more target microRNAs is measured in the subject. The level of the one or more target microRNAs in a reference subject can be a reference level.

The plurality of different times can comprise two or more times 1, 2, 3, 4, 5, 10, 15, 20, 25, 28, 30, 35, 40, 45, 50, 55, 60, 65, 70, 75, 80, 85, and 90 days following a known or suspected myocardial infarction in the subject. The plurality of different times can comprise two or more times 2, 5, 28, and 90 days following a known or suspected myocardial infarction in the subject. The temporal pattern of the level of the one or more target microRNAs can indicate that the subject suffered a myocardial infarction. The temporal pattern of the level of the one or more target microRNAs can indicate how long ago the subject suffered the myocardial infarction.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

DETAILED DESCRIPTION OF THE INVENTION

Figure 1:
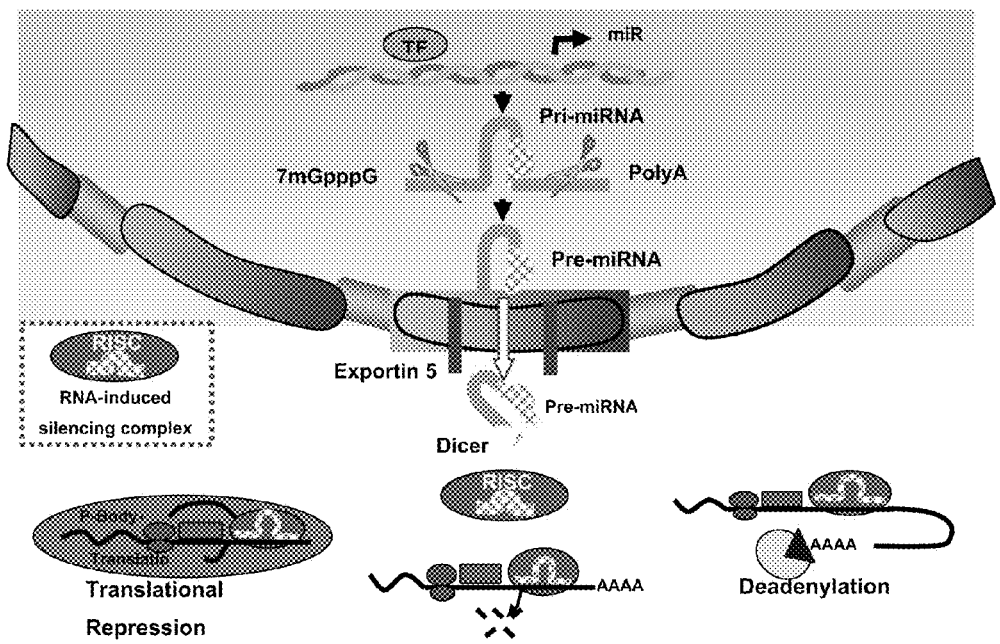
FIG. 1 is a diagram showing production and function of microRNA.
Figure 2:
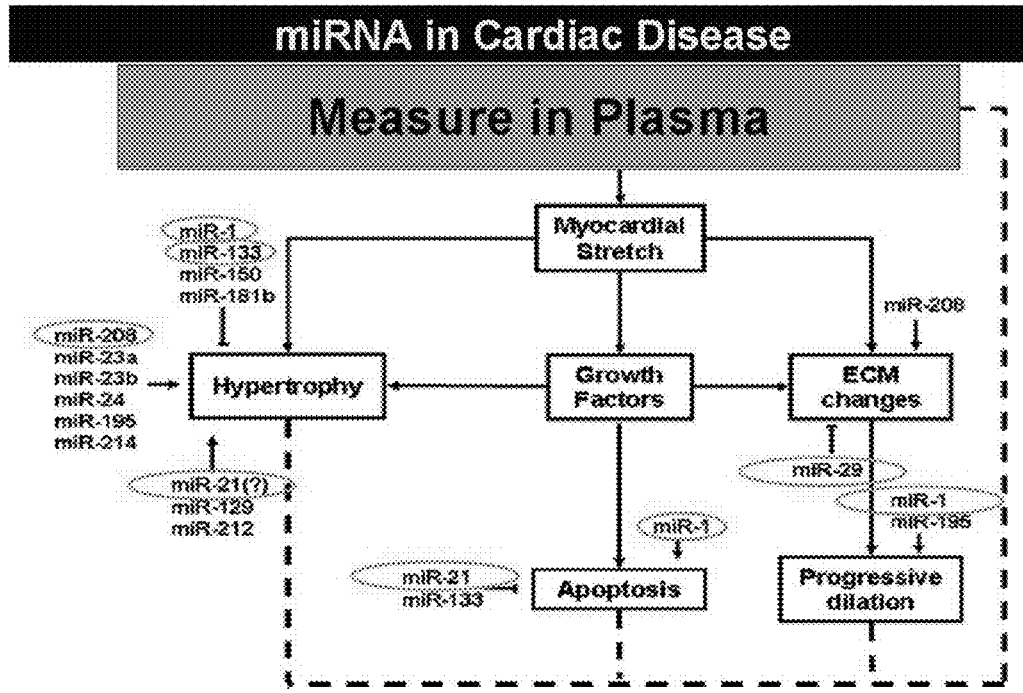
FIG. 2 is a chart showing micro RNAs involved in heart disease.
Figure 3:
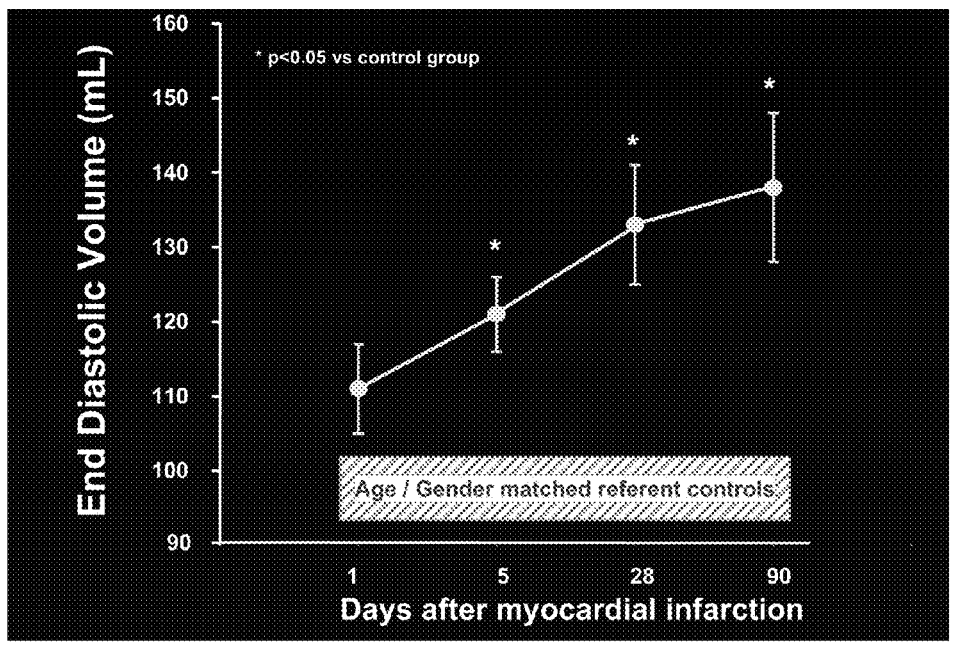
FIG. 3 is a graph of end diastolic volume (EDV) versus days after myocardial infarction. EDV increases while EDV of age and gender matched referent controls does not.
Figure 4:
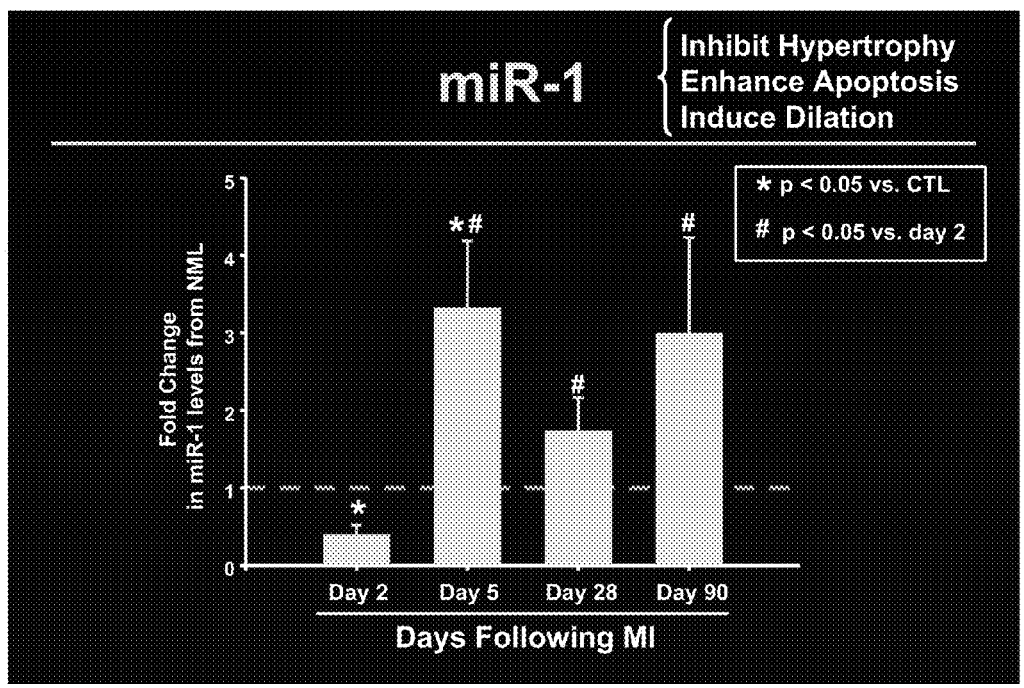
FIG. 4 is a graph of the fold change of miR-1 (compared to age matched normals) versus days following myocardial infarction.
Figure 5:
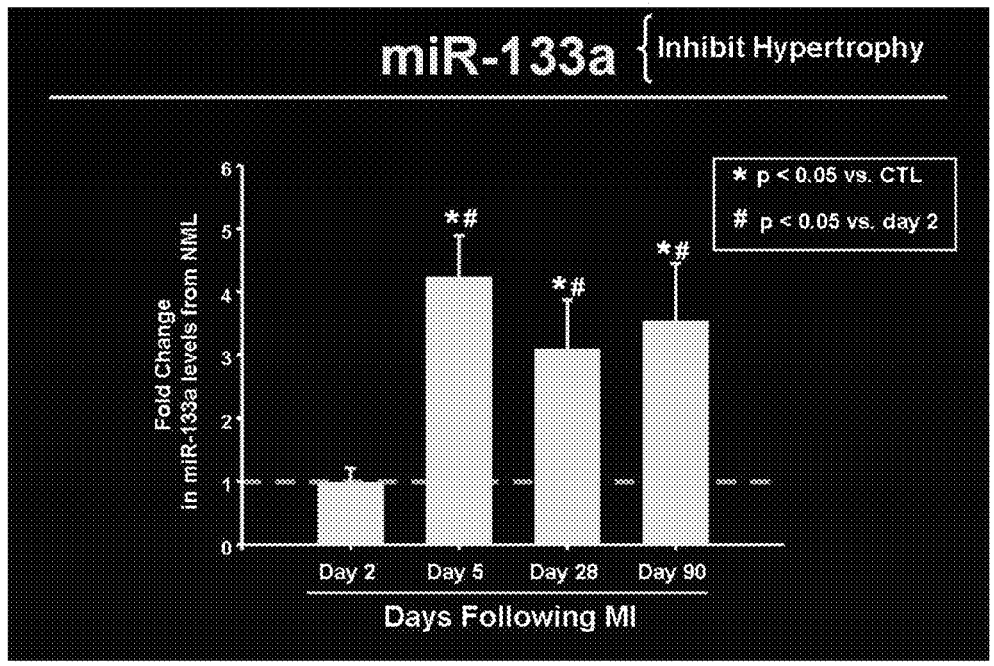
FIG. 5 is a graph of the fold change of miR-133a (compared to age matched normals) versus days following myocardial infarction.
Figure 6:
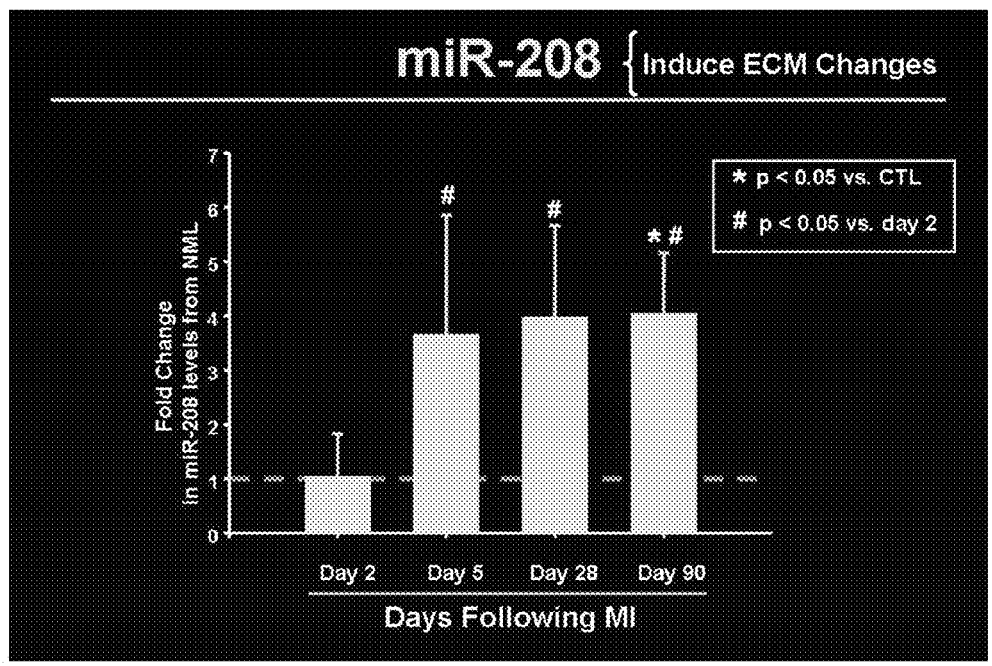
FIG. 6 is a graph of the fold change of miR-208 (compared to age matched normals) versus days following myocardial infarction.
Figure 7:
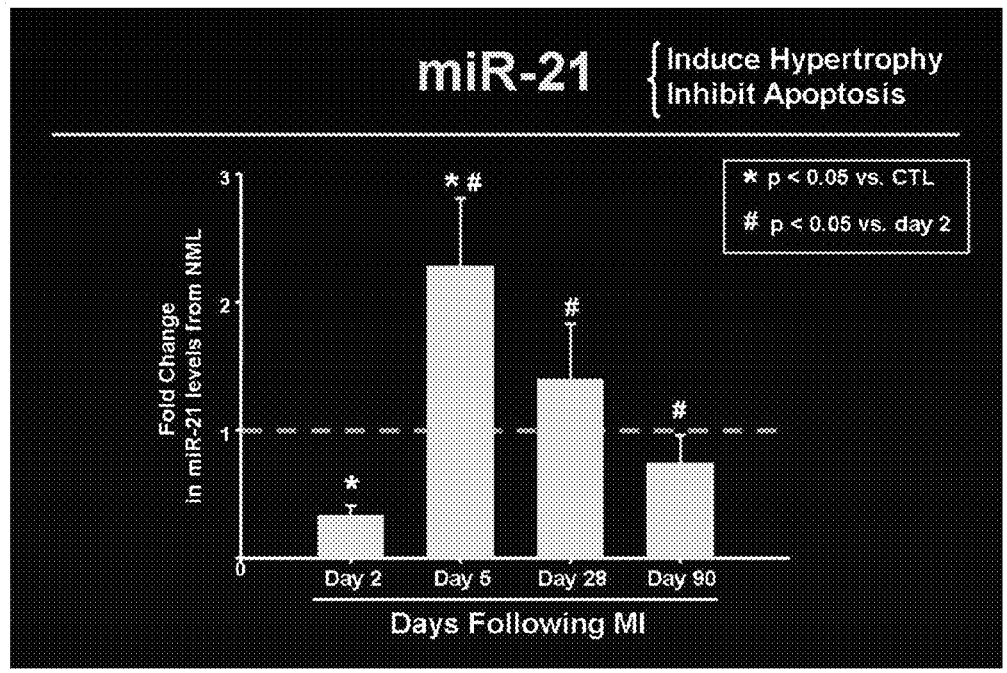
FIG. 7 is a graph of the fold change of miR-21 (compared to age matched normals) versus days following myocardial infarction.
Figure 8:
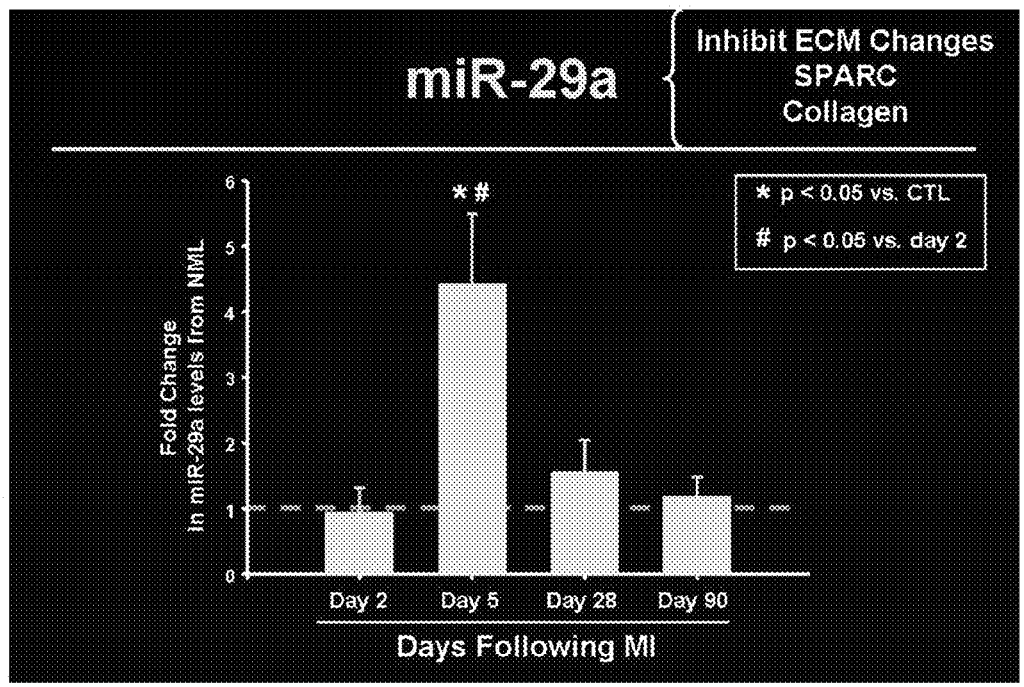
FIG. 8 is a graph of the fold change of miR-29a (compared to age matched normals) versus days following myocardial infarction.

The disclosed method and compositions may be understood more readily by reference to the following detailed description of particular embodiments and the Example included therein and to the Figures and their previous and following description.

Disclosed are methods and materials for assessing cardiac failure, cardiac hypertrophy, and left ventricular remodeling using microRNA levels. The level of microRNAs can be measured in a body fluid, such as plasma and serum. Disclosed is method comprising detecting one or more target microRNAs in a body fluid of a subject at a plurality of different times. The temporal pattern of the level of the one or more target microRNAs can indicates the presence, severity, or a combination of left ventricular remodeling in the subject.

The presence, severity, or a combination of left ventricular remodeling in the subject can be indicated by comparing the temporal pattern of the level of the one or more target microRNAs to one or more reference temporal patterns. The one or more microRNAs can comprise one or more of miR-1, miR-21, miR-23a, miR-29a, miR-30, miR-133a, miR-150, miR-195, miR-199, miR-208, miR-214, and miR-125b. The one or more microRNAs can comprise one or more of miR-1, miR-21, miR-29a, miR-133a, miR-208, and miR-125b. The one or more microRNAs can comprise one or more of miR-1, miR-21, miR-29a, miR-133a, and miR-208.

The body fluid can be, for example, blood, plasma, serum, or lymphatic fluid. The plurality of different times at which the one or more microRNAs are detected can comprise two or more times separated by 1, 2, 3, 4, 5, 10, 15, 20, 23, 24, 25, 26, 27, 28, 30, 35, 40, 45, 50, 55, 60, 62, 65, 70, 75, 80, 85, 86, 87, 88, 89, and 90 days. The plurality of different times at which the one or more microRNAs are detected can comprise two or more times separated by 2, 3, 23, and 62 days. The level of the one or more target microRNAs can comprise the measured level of the one or more target microRNAs normalized to the measured level of a reference RNA in the body fluid. The reference RNA can be snRNA U6.

The level of the one or more target microRNAs can comprise the measured level of the one or more target microRNAs expressed as the fold difference of the measured level of the one or more target microRNAs to the measured level of the one or more target microRNAs in a reference subject. The level of the one or more target microRNAs can comprise the measured level of the one or more target microRNAs normalized to the measured level of a reference RNA in the body fluid expressed as the fold difference of the normalized level of the one or more target microRNAs to the measured level of the one or more target microRNAs in the same body fluid of reference subject normalized to the measured level of a reference RNA in the body fluid of the reference subject.

The level of the one or more target microRNAs in a reference subject can be measured at the same time as the level of the one or more target microRNAs is measured in the subject. The level of the one or more target microRNAs in a reference subject can be measured at a different time than the level of the one or more target microRNAs is measured in the subject. The level of the one or more target microRNAs in a reference subject can be a reference level.

The plurality of different times can comprise two or more times 1, 2, 3, 4, 5, 10, 15, 20, 25, 28, 30, 35, 40, 45, 50, 55, 60, 65, 70, 75, 80, 85, and 90 days following a known or suspected myocardial infarction in the subject. The plurality of different times can comprise two or more times 2, 5, 28, and 90 days following a known or suspected myocardial infarction in the subject. The temporal pattern of the level of the one or more target microRNAs can indicate that the subject suffered a myocardial infarction. The temporal pattern of the level of the one or more target microRNAs can indicate how long ago the subject suffered the myocardial infarction.

MicroRNAs (miRNAs) are noncoding RNAs that bind to target mRNAs and reduce their expression through translational repression or mRNA degradation. Measurements made in myocardial tissue have suggested the miRNAs play a regulatory role in myocardial growth, fibrosis, and remodeling. However, whether specific temporal changes in miRNAs occur in patients during the left ventricular (LV) remodeling process that follows myocardial infarction (MI) has not previously been demonstrated.

It has been discovered that miRNAs relevant to cardiac disease, including left ventricular remodeling, can be reliably measured in body fluids such as plasma and serum, that the levels of these miRNAs follow temporal patterns following myocardial infarction and during remodeling, and that these temporal patterns are highly correlated to the severity of left ventricular remodeling. Based on this, the disclosed methods for assessing cardiac failure, cardiac hypertrophy, and left ventricular remodeling using microRNA levels have been developed.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Materials

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a microRNA measurement is disclosed and discussed and a number of modifications that can be made to the method are discussed, each and every combination and permutation of the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Primers

Primers for use in the disclosed methods can be oligonucleotides having sequence complementary to the target sequence. This sequence is referred to as the complementary portion of the primer. The complementary portion of a primer can be any length that supports specific and stable hybridization between the primer and the target sequence. Generally this is 10 to 35 nucleotides long, but is preferably 16 to 24 nucleotides long. For whole genome amplification, it is preferred that the primers are from 12 to 60 nucleotides long.

B. Conformation Dependent Labels

Conformation dependent labels refer to all labels that produce a change in fluorescence intensity or wavelength based on a change in the form or conformation of the molecule or compound with which the label is associated. Examples of conformation dependent labels used in the context of probes and primers include molecular beacons, Amplifluors, FRET probes, cleavable FRET probes, TaqMan probes, scorpion primers, fluorescent triplex oligos including but not limited to triplex molecular beacons or triplex FRET probes, fluorescent water-soluble conjugated polymers, PNA probes and QPNA probes. Such labels, and, in particular, the principles of their function, can be adapted for use with the disclosed methods. Several types of conformation dependent labels are reviewed in Schweitzer and Kingsmore, Curr. Opin. Biotech. 12:21-27 (2001).

Stem quenched labels, a form of conformation dependent labels, are fluorescent labels positioned on a nucleic acid such that when a stem structure forms a quenching moiety is brought into proximity such that fluorescence from the label is quenched. When the stem is disrupted, the quenching moiety is no longer in proximity to the fluorescent label and fluorescence increases. Examples of this effect can be found in molecular beacons, fluorescent triplex oligos, triplex molecular beacons, triplex FRET probes, and QPNA probes, the operational principles of which can be adapted for use with the disclosed methods.

Stem activated labels, a form of conformation dependent labels, are labels or pairs of labels where fluorescence is increased or altered by formation of a stem structure. Stem activated labels can include an acceptor fluorescent label and a donor moiety such that, when the acceptor and donor are in proximity (when the nucleic acid strands containing the labels form a stem structure), fluorescence resonance energy transfer from the donor to the acceptor causes the acceptor to fluoresce. Stem activated labels are typically pairs of labels positioned on nucleic acid molecules such that the acceptor and donor are brought into proximity when a stem structure is formed in the nucleic acid molecule. If the donor moiety of a stem activated label is itself a fluorescent label, it can release energy as fluorescence (typically at a different wavelength than the fluorescence of the acceptor) when not in proximity to an acceptor (that is, when a stem structure is not formed). When the stem structure forms, the overall effect would then be a reduction of donor fluorescence and an increase in acceptor fluorescence. FRET probes are an example of the use of stem activated labels, the operational principles of which can be adapted for use with the disclosed methods.

C. Detection Labels

To aid in detection and quantitation of microRNAs, detection labels can be incorporated into detection probes or detection molecules or directly incorporated into amplied nucleic acids. As used herein, a detection label is any molecule that can be associated with nucleic acid, directly or indirectly, and which results in a measurable, detectable signal, either directly or indirectly. Many such labels are known to those of skill in the art. Examples of detection labels suitable for use in the disclosed method are radioactive isotopes, fluorescent molecules, phosphorescent molecules, enzymes, antibodies, and ligands.

Examples of suitable fluorescent labels include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as Quantum Dye®, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH$_3$, Diamino Phenyl Oxydiazole (DAO), Dimethylamino-5-Sulphonic acid, Dipyrromethenboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine 6G, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Useful fluorescent labels are fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7',8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio.

Additional labels of interest include those that provide for signal only when the probe with which they are associated is specifically bound to a target molecule, where such labels include: "molecular beacons" as described in Tyagi & Kramer, Nature Biotechnology (1996) 14:303 and EP 0 070 685 B1. Other labels of interest include those described in U.S. Pat. No. 5,563,037; WO 97/17471 and WO 97/17076.

Labeled nucleotides are a useful form of detection label for direct incorporation into expressed nucleic acids during synthesis. Examples of detection labels that can be incorporated into nucleic acids include nucleotide analogs such as BrdUrd (5-bromodeoxyuridine, Hoy and Schimke, *Mutation Research* 290:217-230 (1993)), aminoallyldeoxyuridine (Henegariu et al., *Nature Biotechnology* 18:345-348 (2000)), 5-methylcytosine (Sano et al., *Biochim. Biophys. Acta* 951: 157-165 (1988)), bromouridine (Wansick et al., *J. Cell Biology* 122:283-293 (1993)) and nucleotides modified with biotin (Langer et al., *Proc. Natl. Acad. Sci.* USA 78:6633 (1981)) or with suitable haptens such as digoxygenin (Kerkhof, *Anal. Biochem.* 205:359-364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.*, 22:3226-3232 (1994)). A preferred nucleotide analog detection label for DNA is BrdUrd (bromodeoxyuridine, BrdUrd, BrdU, BUdR, Sigma-Aldrich Co.). Other useful nucleotide analogs for incorporation of detection label into DNA are AA-dUTP (aminoallyl-deoxyuridine triphosphate, Sigma-Aldrich Co.), and 5-methyl-dCTP (Roche Molecular Biochemicals). A useful nucleotide analog for incorporation of detection label into RNA is biotin-16-UTP (biotin-6-uridine-5'-triphosphate, Roche Molecular Biochemicals). Fluorescein, Cy3, and Cy5 can be linked to dUTP for direct labeling. Cy3.5 and Cy7 are available as avidin or anti-digoxygenin conjugates for secondary detection of biotin- or digoxygenin-labeled probes.

Detection labels that are incorporated into nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5-chloro)tricyclo [3.3.1.1$^{3,7}$]decane]-4-yl)phenyl phosphate; Tropix, Inc.). Labels can also be enzymes, such as alkaline phosphatase, soybean peroxidase, horseradish peroxidase and polymerases, that can be detected, for example, with chemical signal amplification or by using a substrate to the enzyme which produces light (for example, a chemiluminescent 1,2-dioxetane substrate) or fluorescent signal.

Molecules that combine two or more of these detection labels are also considered detection labels. Any of the known detection labels can be used with the disclosed probes, tags, molecules and methods to label and detect microRNAs or nucleic acid produced in the disclosed methods. Methods for detecting and measuring signals generated by detection labels are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. As used herein, detection molecules are molecules which interact with a compound or composition to be detected and to which one or more detection labels are coupled.

D. Sequence Similarities

It is understood that as discussed herein the use of the terms homology and identity mean the same thing as similarity. Thus, for example, if the use of the word homology is used between two sequences (non-natural sequences, for example) it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed microRNAs herein, is through defining the variants and derivatives in terms of homology to specific known sequences. This identity of particular sequences disclosed herein is also discussed elsewhere herein. In general, variants of microRNAs herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to a stated sequence or a native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods can differ, but the skilled artisan understands if identity is found with at least one of these methods, the sequences would be said to have the stated identity.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

E. Hybridization and Selective Hybridization

The term hybridization typically means a sequence driven interaction between at least two nucleic acid molecules, such as a primer or a probe and a microRNA. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization can involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting nucleic acid is in for example, 10 or 100 or 1000 fold excess. This type of assay can be performed at under conditions where both the limiting and non-limiting nucleic acids are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of nucleic acid that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the nucleic acid is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the nucleic acid molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions can provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

F. Nucleic Acids

There are a variety of molecules disclosed herein that are nucleic acid based, including, for example, microRNAs. The disclosed nucleic acids can be made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if a nucleic acid molecule is introduced into a cell or cell environment through for example exogenous delivery, it is advantageous that the nucleic acid molecule be made up of nucleotide analogs that reduce the degradation of the nucleic acid molecule in the cellular environment.

So long as their relevant function is maintained, primers, probes, and any other oligonucleotides and nucleic acids can be made up of or include modified nucleotides (nucleotide analogs). Many modified nucleotides are known and can be used in oligonucleotides and nucleic acids. A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl, hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Other modified bases are those that function as universal bases. Universal bases include 3-nitropyrrole and 5-nitroindole. Universal bases substitute for the normal bases but have no bias in base pairing. That is, universal bases can base pair with any other base. Base modifications often can be combined with for example a sugar modification, such as 2'-O-methoxyethyl, to achieve unique properties such as increased duplex stability. There are numerous United States patents such as U.S. Pat. Nos. 4,845, 205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, which detail and describe a range of base modifications. Each of these patents is herein incorporated by reference in its entirety, and specifically for their description of base modifications, their synthesis, their use, and their incorporation into oligonucleotides and nucleic acids.

Nucleotide analogs can also include modifications of the sugar moiety. Modifications to the sugar moiety would include natural modifications of the ribose and deoxyribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted C1 to C10, alkyl or C2 to C10 alkenyl and alkynyl. 2' sugar modifications also include but are not limited to —O[$(CH_2)nO$]m $CH_3$, —O$(CH_2)n$ $OCH_3$, —O$(CH_2)n$ $NH_2$, —O$(CH_2)n$ $CH_3$, —O$(CH_2)n$ —$ONH_2$, and —O$(CH_2)nON$[$(CH_2)n$ $CH_3$]$_2$, where n and m are from 1 to about 10.

Other modifications at the 2' position include but are not limited to: C1 to C10 lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2$ $CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications can also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as $CH_2$ and S. Nucleotide sugar analogs can also have sugar mimetics such as cyclobutyl moieties in place of the pentofuranosyl sugar. There are numerous United States patents that teach the preparation of such modified sugar structures such as U.S. Pat. Nos. 4,981, 957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety, and specifically for their description of modified sugar structures, their synthesis, their use, and their incorporation into nucleotides, oligonucleotides and nucleic acids.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and amino alkylphosphoramidates, thionophosphoramidates, thionoalkylphosphonates, thionoalkylphosphotriesters, and boranophosphates. It is understood that these phosphate or modified phosphate linkages between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference its entirety, and specifically for their description of modified phosphates, their synthesis, their use, and their incorporation into nucleotides, oligonucleotides and nucleic acids.

It is understood that nucleotide analogs need only contain a single modification, but can also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize and hybridize to (base pair to) complementary nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts. Numerous United States patents disclose how to make and use these types of phosphate replacements and include but are not limited to U.S. Pat. Nos. 5,034,506; 5,166,315; 5,185, 444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference its entirety, and specifically for their description of phosphate replacements, their synthesis, their use, and their incorporation into nucleotides, oligonucleotides and nucleic acids.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. (See also Nielsen et al., *Science* 254:1497-1500 (1991)).

Oligonucleotides and nucleic acids can be comprised of nucleotides and can be made up of different types of nucleotides or the same type of nucleotides. For example, one or more of the nucleotides in an oligonucleotide can be ribonucleotides, 2'-O-methyl ribonucleotides, or a mixture of ribonucleotides and 2'-O-methyl ribonucleotides; about 10% to about 50% of the nucleotides can be ribonucleotides, 2'-O-methyl ribonucleotides, or a mixture of ribonucleotides and 2'-O-methyl ribonucleotides; about 50% or more of the nucleotides can be ribonucleotides, 2'-O-methyl ribonucleotides, or a mixture of ribonucleotides and 2'-O-methyl ribonucleotides; or all of the nucleotides are ribonucleotides, 2'-O-methyl ribonucleotides, or a mixture of ribonucleotides and 2'-O-methyl ribonucleotides. Such oligonucleotides and nucleic acids can be referred to as chimeric oligonucleotides and chimeric nucleic acids.

G. Solid Supports

Solid supports are solid-state substrates or supports with which molecules (such as probes) or other components used in, or produced by, the disclosed methods can be associated. Molecules can be associated with solid supports directly or indirectly. For example, probes can be bound to the surface of a solid support. An array is a solid support to which multiple probes or other molecules have been associated in an array, grid, or other organized pattern.

Solid-state substrates for use in solid supports can include any solid material with which components can be associated, directly or indirectly. This includes materials such as acrylamide, agarose, cellulose, nitrocellulose, glass, gold, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, and polyamino acids. Solid-state substrates can have any useful form including thin film, membrane, bottles, dishes, fibers, woven fibers, shaped polymers, particles, beads, microparticles, or a combination. Solid-state substrates and solid supports can be porous or non-porous. A chip is a rectangular or square small piece of material. Preferred forms for solid-state substrates are thin films, beads, or chips. A useful form for a solid-state substrate is a microtiter dish. In some embodiments, a multiwell glass slide can be employed.

An array can include a plurality of molecules, compounds or probes immobilized at identified or predefined locations on the solid support. Each predefined location on the solid support generally has one type of component (that is, all the components at that location are the same). Alternatively, multiple types of components can be immobilized in the same predefined location on a solid support. Each location will have multiple copies of the given components. The spatial separation of different components on the solid support allows separate detection and identification.

Although useful, it is not required that the solid support be a single unit or structure. A set of molecules, compounds and/or probes can be distributed over any number of solid supports. For example, at one extreme, each component can be immobilized in a separate reaction tube or container, or on separate beads or microparticles.

Methods for immobilization of oligonucleotides to solid-state substrates are well established. Oligonucleotides, including address probes and detection probes, can be coupled to substrates using established coupling methods. For example, suitable attachment methods are described by Pease et al., *Proc. Natl. Acad. Sci.* USA 91(11):5022-5026 (1994), and Khrapko et al., *Mol Biol* (Mosk) (USSR) 25:718-730 (1991). A method for immobilization of 3'-amine oligonucleotides on casein-coated slides is described by Stimpson et al., *Proc. Natl. Acad. Sci.* USA 92:6379-6383 (1995). A useful method of attaching oligonucleotides to solid-state substrates is described by Guo et al., *Nucleic Acids Res.* 22:5456-5465 (1994).

Each of the components immobilized on the solid support can be located in a different predefined region of the solid support. The different locations can be different reaction chambers. Each of the different predefined regions can be physically separated from each other of the different regions. The distance between the different predefined regions of the solid support can be either fixed or variable. For example, in an array, each of the components can be arranged at fixed distances from each other, while components associated with beads will not be in a fixed spatial relationship. In particular, the use of multiple solid support units (for example, multiple beads) will result in variable distances.

Components can be associated or immobilized on a solid support at any density. Components can be immobilized to the solid support at a density exceeding 400 different components per cubic centimeter. Arrays of components can have any number of components. For example, an array can have at least 1,000 different components immobilized on the solid support, at least 10,000 different components immobilized on the solid support, at least 100,000 different components immobilized on the solid support, or at least 1,000,000 different components immobilized on the solid support.

H. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for detecting and measuring microRNAs, the kit comprising amplification primers and detection probes. The kits also can contain enzymes and reaction solutions.

I. Mixtures

Disclosed are mixtures formed by performing or preparing to perform the disclosed method. For example, disclosed are mixtures comprising a body fluid and amplification primers, microRNA and amplification primers, and amplified microRNA and detection probes.

Whenever the method involves mixing or bringing into contact compositions or components or reagents, performing the method creates a number of different mixtures. For example, if the method includes 3 mixing steps, after each one of these steps a unique mixture is formed if the steps are performed separately. In addition, a mixture is formed at the completion of all of the steps regardless of how the steps were performed. The present disclosure contemplates these mixtures, obtained by the performance of the disclosed methods as well as mixtures containing any disclosed reagent, composition, or component, for example, disclosed herein.

J. Systems

Disclosed are systems useful for performing, or aiding in the performance of, the disclosed method. Systems generally comprise combinations of articles of manufacture such as structures, machines, devices, and the like, and compositions, compounds, materials, and the like. Such combinations that are disclosed or that are apparent from the disclosure are contemplated. For example, disclosed and contemplated are systems comprising microRNAs and a detection apparatus.

K. Data Structures and Computer Control

Disclosed are data structures used in, generated by, or generated from, the disclosed method. Data structures generally are any form of data, information, and/or objects collected, organized, stored, and/or embodied in a composition or medium. A temporal pattern of microRNA levels stored in electronic form, such as in RAM or on a storage disk, is a type of data structure.

The disclosed method, or any part thereof or preparation therefor, can be controlled, managed, or otherwise assisted by computer control. Such computer control can be accomplished by a computer controlled process or method, can use and/or generate data structures, and can use a computer program. Such computer control, computer controlled processes, data structures, and computer programs are contemplated and should be understood to be disclosed herein.

A. Actions Based on Identifications

The disclosed methods include the determination, identification, indication, correlation, diagnosis, prognosis, etc. (which can be referred to collectively as "identifications") of subjects, diseases, conditions, states, etc. based on measurements, detections, comparisons, analyses, assays, screenings, etc. For example, levels or amounts of microRNAs can be used to identify subjects that have or are at risk of myocardial infarction, left ventricular remodeling, left ventricular hypertrophy, diastolic heart failure, aortic aneurysm, ischemia, and/or electrical stimulation. Such identifications are useful for many reasons. For example, and in particular, such identifications allow specific actions to be taken based on, and relevant to, the particular identification made. For example, diagnosis of a particular disease or condition in particular subjects (and the lack of diagnosis of that disease or condition in other subjects) has the very useful effect of identifying subjects that would benefit from treatment, actions, behaviors, etc. based on the diagnosis. For example, treatment for a particular disease or condition in subjects identified is significantly different from treatment of all subjects without making such an identification (or without regard to the identification). Subjects needing or that could benefit from the treatment will receive it and subjects that do not need or would not benefit from the treatment will not receive it.

Accordingly, also disclosed herein are methods comprising taking particular actions following and based on the disclosed identifications. For example, disclosed are methods comprising creating a record of an identification (in physical—such as paper, electronic, or other—form, for example). Thus, for example, creating a record of an identification based on the disclosed methods differs physically and tangibly from merely performing a measurement, detection, comparison, analysis, assay, screen, etc. Such a record is particularly substantial and significant in that it allows the identification to be fixed in a tangible form that can be, for example, communicated to others (such as those who could treat, monitor, follow-up, advise, etc. the subject based on the identification); retained for later use or review; used as data to assess sets of subjects, treatment efficacy, accuracy of identifications based on different measurements, detections, comparisons, analyses, assays, screenings, etc., and the like. For example, such uses of records of identifications can be made, for example, by the same individual or entity as, by a different individual or entity than, or a combination of the same individual or entity as and a different individual or entity than, the individual or entity that made the record of the identification. The disclosed methods of creating a record can be combined with any one or more other methods disclosed herein, and in particular, with any one or more steps of the disclosed methods of identification.

As another example, disclosed are methods comprising making one or more further identifications based on one or more other identifications. For example, particular treatments, monitorings, follow-ups, advice, etc. can be identified based on the other identification. For example, identification of subject as having a disease or condition with a high level of a particular component can be further identified as a subject that could or should be treated with a therapy based on or directed to the high level component. A record of such further identifications can be created (as described above, for example) and can be used in any suitable way. Such further identifications can be based, for example, directly on the other identifications, a record of such other identifications, or a combination. Such further identifications can be made, for example, by the same individual or entity as, by a different individual or entity than, or a combination of the same individual or entity as and a different individual or entity than, the individual or entity that made the other identifications. The disclosed methods of making a further identification can be combined with any one or more other methods disclosed herein, and in particular, with any one or more steps of the disclosed methods of identification.

As another example, disclosed are methods comprising treating, monitoring, following-up with, advising, etc. a subject identified in any of the disclosed methods.

Also disclosed are methods comprising treating, monitoring, following-up with, advising, etc. a subject for which a record of an identification from any of the disclosed methods has been made. For example, particular treatments, monitorings, follow-ups, advice, etc. can be used based on an identification and/or based on a record of an identification. For example, a subject identified as having a disease or condition with a high level of a particular component (and/or a subject for which a record has been made of such an identification) can be treated with a therapy based on or directed to the high level component. Such treatments, monitorings, follow-ups, advice, etc. can be based, for example, directly on identifications, a record of such identifications, or a combination. Such treatments, monitorings, follow-ups, advice, etc. can be performed, for example, by the same individual or entity as, by a different individual or entity than, or a combination of the same individual or entity as and a different individual or entity than, the individual or entity that made the identifications and/or record of the identifications. The disclosed methods of treating, monitoring, following-up with, advising, etc. can be combined with any one or more other methods disclosed herein, and in particular, with any one or more steps of the disclosed methods of identification.

Uses

The disclosed methods and compositions are applicable to numerous areas including, but not limited to, diagnose, assess prognosis, monitor improvement or deterioration, or monitor the progress of treatment of myocardial infarction, cardiac failure, cardiac hypertrophy, left ventricular remodeling, or a combination. Other uses include determining if and when a myocardial infarction occurred. Other uses are disclosed, apparent from the disclosure, and/or will be understood by those in the art.

Method

Disclosed are methods and materials for assessing cardiac failure, cardiac hypertrophy, and left ventricular remodeling using microRNA levels. The level of microRNAs can be measured in a body fluid, such as plasma and serum. Disclosed is method comprising detecting one or more target microRNAs in a body fluid of a subject at a plurality of different times. The temporal pattern of the level of the one or more target microRNAs can indicates the presence, severity, or a combination of left ventricular remodeling in the subject.

The presence, severity, or a combination of left ventricular remodeling in the subject can be indicated by comparing the temporal pattern of the level of the one or more target microRNAs to one or more reference temporal patterns. The one or more microRNAs can comprise one or more of miR-1, miR-21, miR-23a, miR-29a, miR-30, miR-133a, miR-150, miR-195, miR-199, miR-208, miR-214, and miR-125b. The one or more microRNAs can comprise one or more of miR-1, miR-21, miR-29a, miR-133a, miR-208, and miR-125b. The one or more microRNAs can comprise one or more of miR-1, miR-21, miR-29a, miR-133a, and miR-208.

The body fluid can be, for example, blood, plasma, serum, or lymphatic fluid. The plurality of different times at which the one or more microRNAs are detected can comprise two or more times separated by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 61, 62, 63, 64, 65, 70, 75, 80, 81, 82, 83, 84 85, 86, 87, 88, 89, and 90 days. The plurality of different times at which the one or more microRNAs are detected can comprise two or more times separated by 1, 2, 3, 4, 5, 10, 15, 20, 23, 24, 25, 26, 27, 28, 30, 35, 40, 45, 50, 55, 60, 62, 65, 70, 75, 80, 85, 86, 87, 88, 89, and 90 days. The plurality of different times at which the one or more microRNAs are detected can comprise two or more times separated by 2, 3, 23, and 62 days. The plurality of different times at which the one or more microRNAs are detected can comprise two or more times that are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 61, 62, 63, 64, 65, 70, 75, 80, 81, 82, 83, 84 85, 86, 87, 88, 89, and 90 days following a known or suspected myocardial infarction. The plurality of different times at which the one or more microRNAs are detected can comprise two or more times that are 1, 2, 3, 4, 5, 10, 15, 20, 23, 24, 25, 26, 27, 28, 30, 35, 40, 45, 50, 55, 60, 62, 65, 70, 75, 80, 85, 86, 87, 88, 89, and 90 days following a known or suspected myocardial infarction. The plurality of different times at which the one or more microRNAs are detected can comprise two or more times that are 2, 3, 23, and 62 days following a known or suspected myocardial infarction. The level of the one or more target microRNAs can comprise the measured level of the one or more target microRNAs normalized to the measured level of a reference RNA in the body fluid. The reference RNA can be snRNA U6.

The level of the one or more target microRNAs can comprise the measured level of the one or more target microRNAs expressed as the fold difference of the measured level of the one or more target microRNAs to the measured level of the one or more target microRNAs in a reference subject. The level of the one or more target microRNAs can comprise the measured level of the one or more target microRNAs normalized to the measured level of a reference RNA in the body fluid expressed as the fold difference of the normalized level of the one or more target microRNAs to the measured level of the one or more target microRNAs in the same body fluid of reference subject normalized to the measured level of a reference RNA in the body fluid of the reference subject.

The level of the one or more target microRNAs in a reference subject can be measured at the same time as the level of the one or more target microRNAs is measured in the subject. The level of the one or more target microRNAs in a reference subject can be measured at a different time than the level of the one or more target microRNAs is measured in the subject. The level of the one or more target microRNAs in a reference subject can be a reference level.

The plurality of different times can comprise two or more times 1, 2, 3, 4, 5, 10, 15, 20, 25, 28, 30, 35, 40, 45, 50, 55, 60, 65, 70, 75, 80, 85, and 90 days following a known or suspected myocardial infarction in the subject. The plurality of different times can comprise two or more times 2, 5, 28, and 90 days following a known or suspected myocardial infarction in the subject. The temporal pattern of the level of the one or more target microRNAs can indicate that the subject suffered a myocardial infarction. The temporal pattern of the level of the one or more target microRNAs can indicate how long ago the subject suffered the myocardial infarction.

Examples of temporal patterns of microRNAs following myocardial infarction are shown in FIGS. 4-8, 26, and 27. For example, a level or amount in a subject of miR-1, miR-208, miR-133a, miR-21, miR-29a, or a combination, higher than the level or amount in control, reference, and/or normal subjects and/or in a control or reference RNA in the subject or in control, reference, and/or normal subjects indicates myocardial infarction, left ventricular remodeling, and/or left ventricular hypertrophy. As another example, a level or amount in a subject of miR-29a, higher than the level or amount in control, reference, and/or normal subjects and/or in a control or reference RNA in the subject or in control, reference, and/or normal subjects immediately after a suspected myocardial infarction indicates myocardial infarction, left ventricular remodeling, and/or left ventricular hypertrophy. The reference RNA can be, for example, snRNA U6.

For example, example, a level or amount in a subject of miR-1, miR-208, miR-133a, miR-21, miR-29a, or a combination, higher than the level or amount in control, reference, and/or normal subjects and/or in a control or reference RNA in the subject or in control, reference, and/or normal subjects followed by a level or amount in the subject of miR-1, miR-21, miR-29a, miR-133a, miR-760, or a combination, lower than the level or amount of miR-1, miR-21, miR-29a, miR-133a, miR-760, respectively, indicates development of diastolic heart failure. As another example, example, in a subject with left ventricular remodeling but not diastolic heart failure, a level or amount in the subject of miR-1, miR-21, miR-29a, miR-133a, miR-760, or a combination, lower than the level or amount of miR-1, miR-21, miR-29a, miR-133a, miR-760, respectively, measured earlier in the subject indicates development of diastolic heart failure.

MicroRNAs can also be used to assess or diagnose aortic aneurysm. For example, a level or amount in a subject of miR-133a, miR-21, miR-29a, miR-208, or a combination, lower than the level or amount in control, reference, and/or normal subjects and/or in a control or reference RNA in the subject or in control, reference, and/or normal subjects indicates aortic aneurysm. The control or reference level can be, for example, the level in normal aorta.

EXAMPLES

B. Example 1

Temporal Patterns of miRNA in Plasma Following Myocardial Infarction

Left ventricular (LV) end-diastolic volume (EDV) was measured by echocardiography on day 1, day 28, and day 90 post-MI. Plasma miRNAs were measured in age matched normal (NML, n=6) and post-MI patients (n=12) from day 2 to day 90 post-MI. All MI patients received standard therapy. Day 1 measurements were preformed within 72 hours of MI. The peak troponin was 167±31. ANOVA and prcomp pairwise on log transformed data.

Plasma RNA (100 uL) was isolated and miRNA reverse transcription for stem loop primers corresponding to specific miRNAs was performed. The miRNAs measured were miR-1, miR-21, miR-29a, miR-125b, miR-133a, and miR-208. The resultant cDNA was subjected to pre-amplification (10 cycles) and corresponding miRNA real-time primers. RT-PCR was performed and data normalized to endogenous snRNA U6. This approach provided high sensitivity, linearity, and reproducibility. Following myocardial infarction, Left ventricular end-diastolic volume (LV EDV) increased progressively compared to the age matched normals. This was accompanied by time dependent changes in specific miRNAs (Table 1). For example, miRNA initially fell at 2 days post-MI, then increased 2-fold over the age matched normals 5 days post-MI, and returned to the level of age matched normals 90 days post-MI. In contrast, miR-133a and miR-208 increased 5 days post-MI and remained elevated 90 days post-MI.

Determinants of LV remodeling include insufficient or maladaptive hypertrophy, increase apoptosis, and altered extracellular matrix structure. MicroRNAs are small noncoding RNAS (approximately 22 nucleotides long) that control gene expression. The miRNAS target mRNA for degradation and/or translational repression. MicroRNAs are important regulators of normal growth and disease dependent altered growth regulation. The disclosed methods represent a sensitive, reliable method to measure miRNAs in plasma, measure serial or temporal changes in specific miRNAs following a myocardial infarction, and assess the temporal relationship between changes in miRNAs and LV remodeling in patients following a myocardial infarction.

Figure 11:
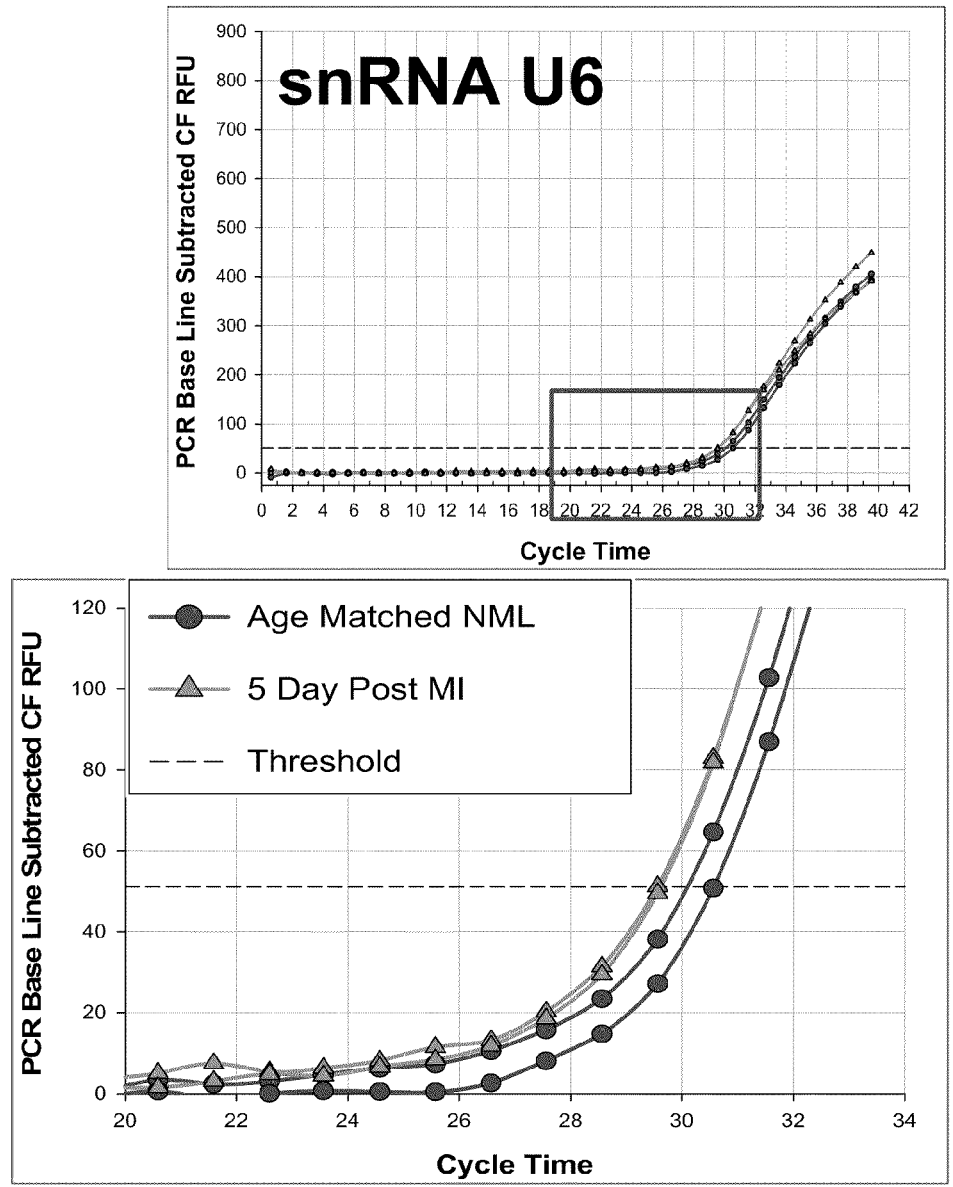
FIG. 11 is a graph of quantitative PCR production of snRNA U6 from patients 5 days after myocardial infarction and age matched normals. Lower panel is an enlargement of the boxed area in the upper panel.
Figure 12:
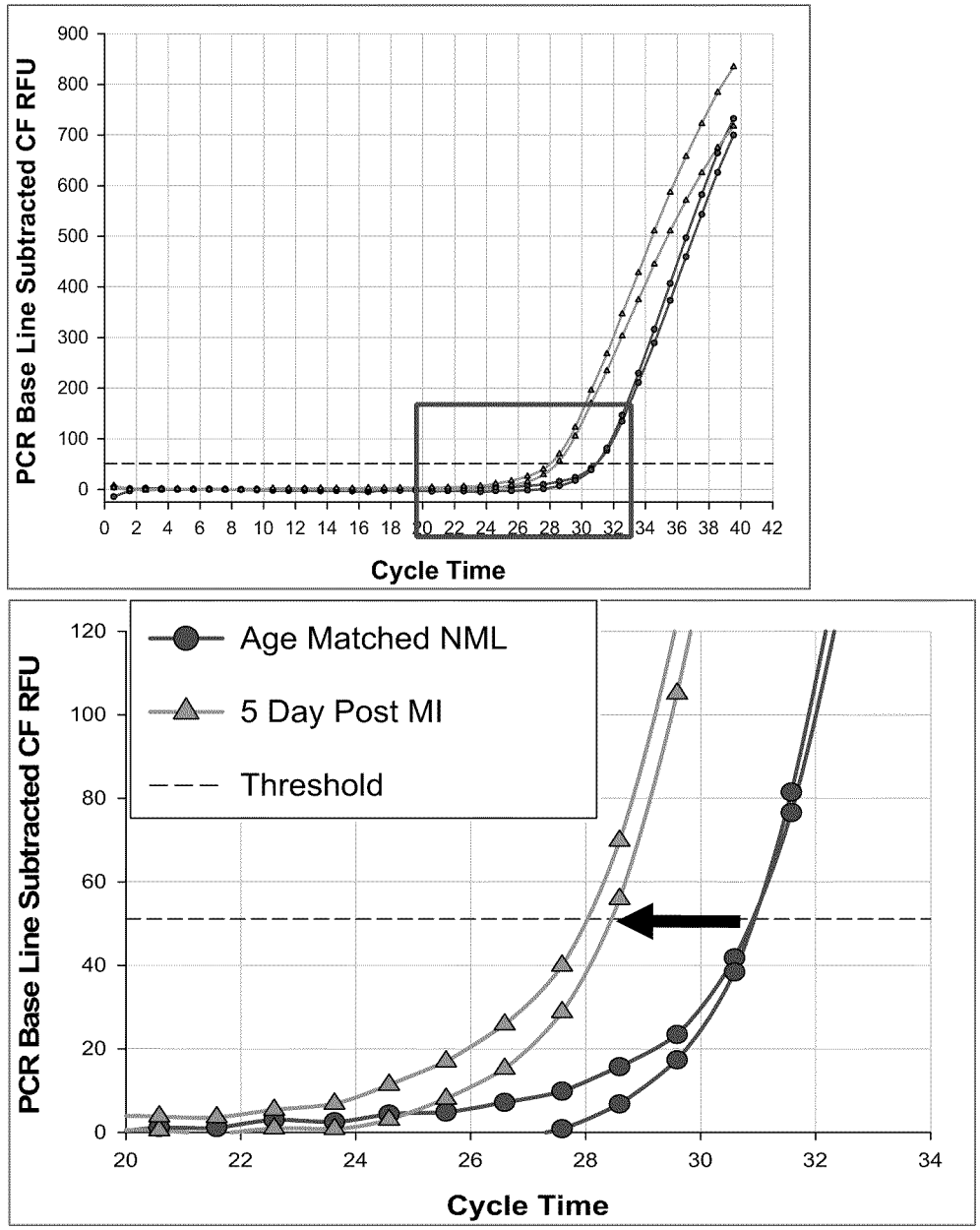
FIG. 12 is a graph of quantitative PCR production of microRNA-1 from patients 5 days after myocardial infarction and age matched normals. Lower panel is an enlargement of the boxed area in the upper panel.
Figure 13:
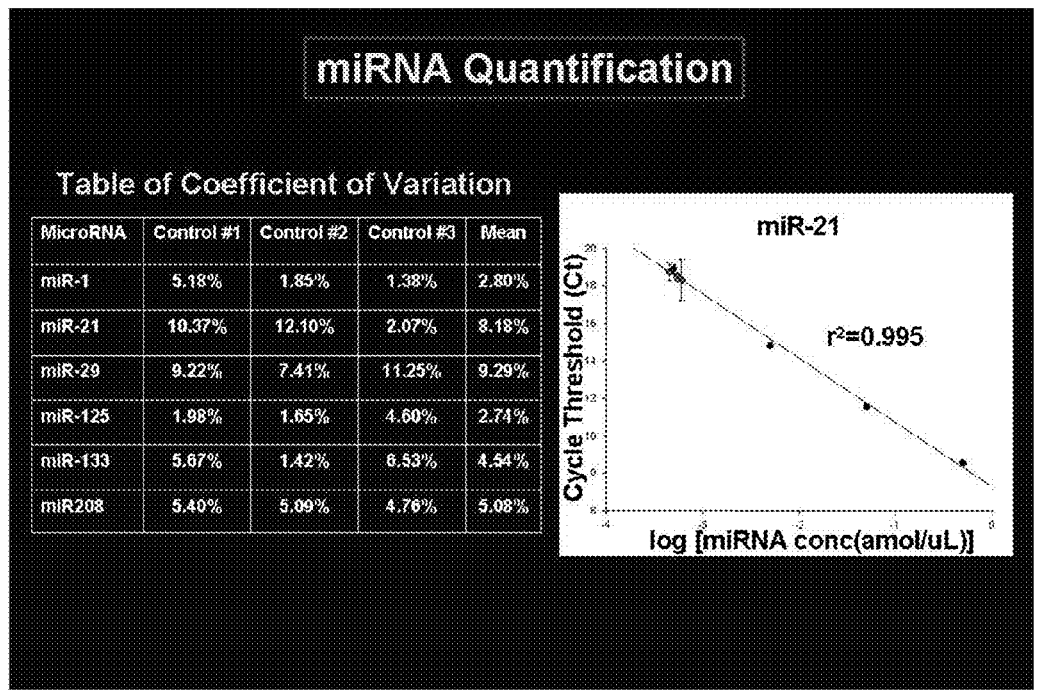
FIG. 13 is a table showing the coefficient of variation in miRNA quantifications for various microRNAs. Also shown is a graph of the correlation line for miR-21.
Figure 14:
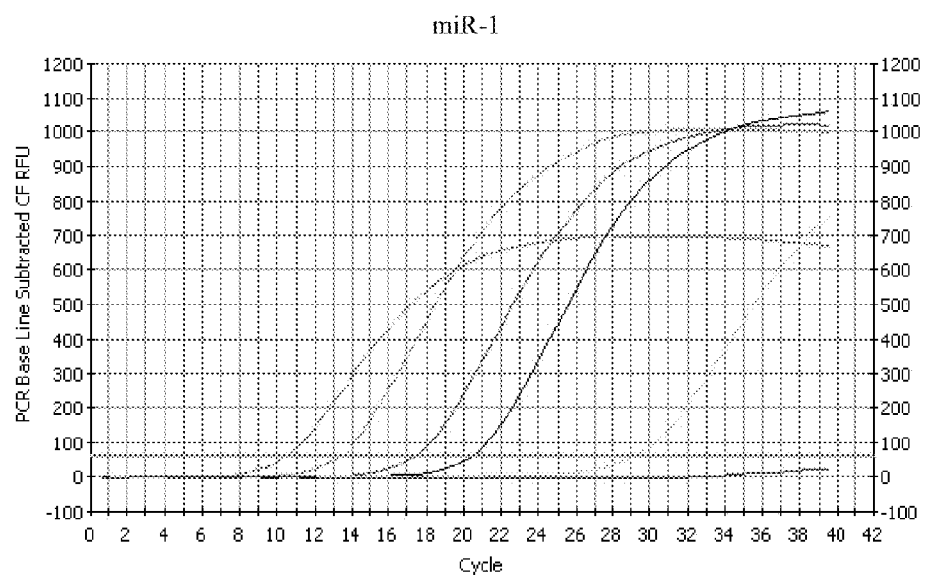
FIG. 14 is a graph of quantitative PCR production of miR-1 versus cycle number for various microRNA samples.
Figure 15:
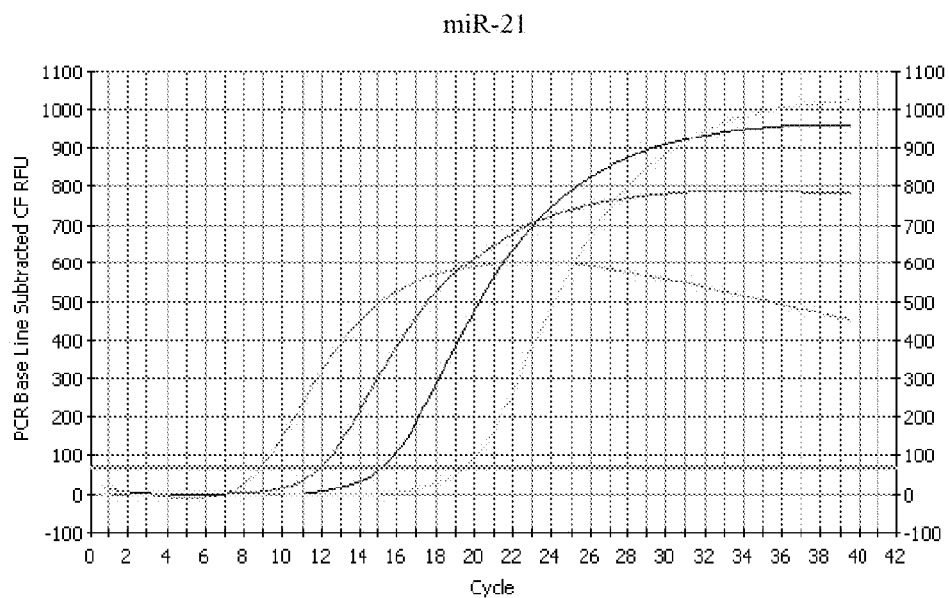
FIG. 15 is a graph of quantitative PCR production of miR-21 versus cycle number for various microRNA samples.
Figure 16:
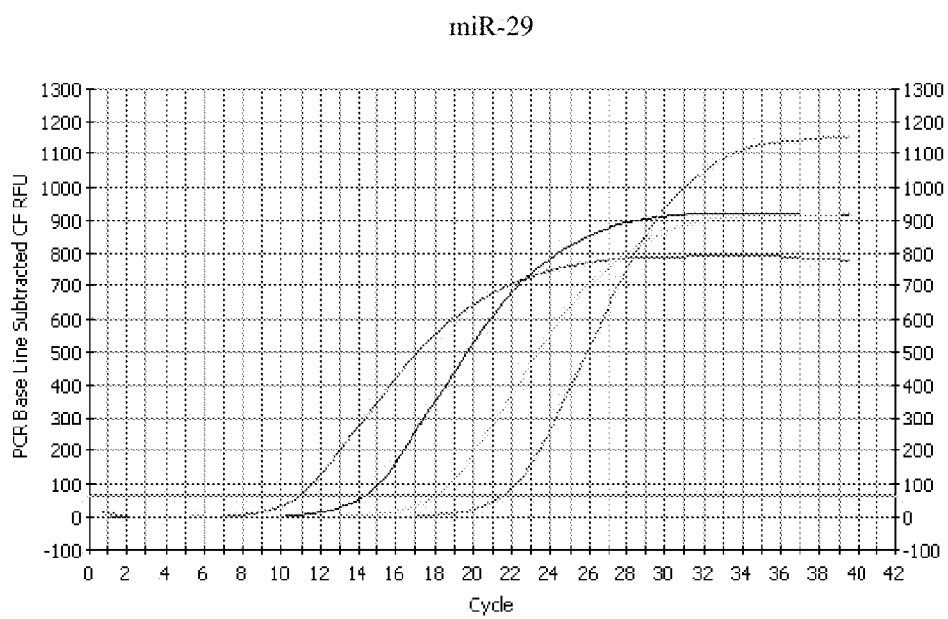
FIG. 16 is a graph of quantitative PCR production of miR-29 versus cycle number for various microRNA samples.
Figure 17:
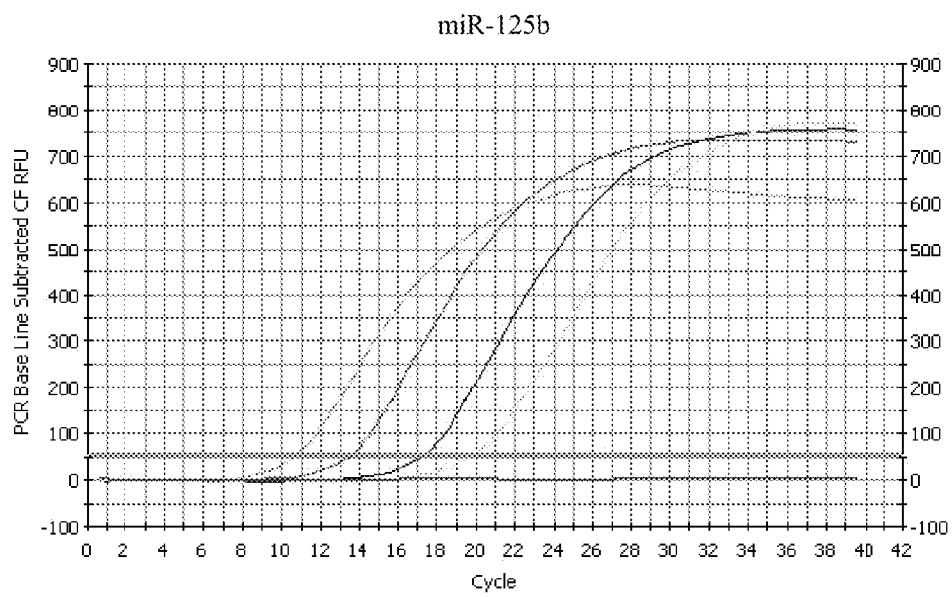
FIG. 17 is a graph of quantitative PCR production of miR-125b versus cycle number for various microRNA samples.
Figure 18:
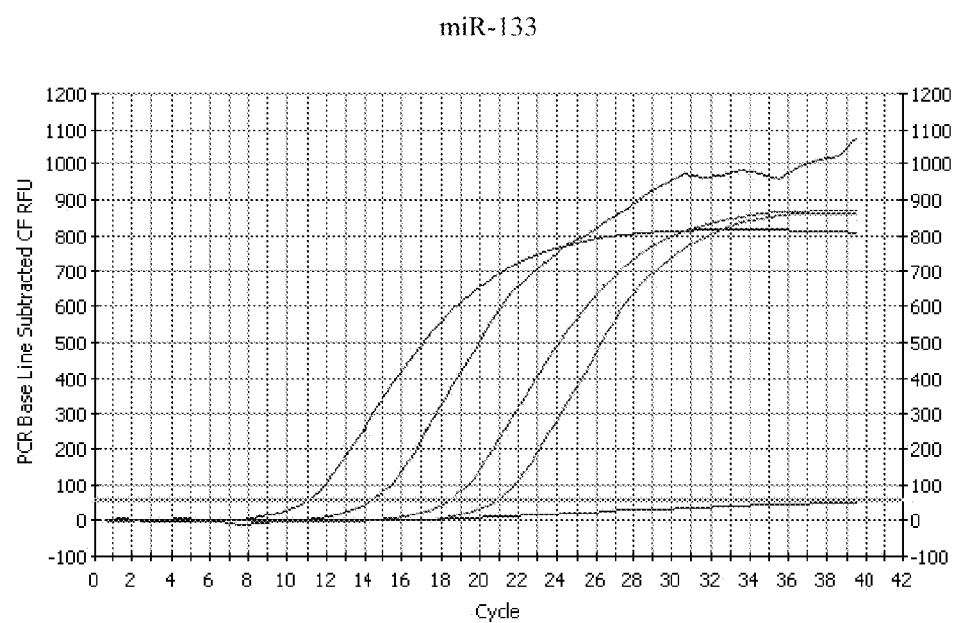
FIG. 18 is a graph of quantitative PCR production of miR-133 versus cycle number for various microRNA samples.

MicroRNA was isolated form plasma by isolating plasma RNA (100 uL) using mirVana Paris kit (Ambion). miRNA was reverse transcribed to cDNA. The cDNA was subjected to a 10-cycle pre-amplification step (Applied Biosystems). Quantitative PCR was then performed using TaqMan primers corresponding to the target (miR-1, miR-21, miR-29a, miR-208, miR-133a) and control (snRNA U6) RNAs. The results are shown in FIGS. 12 and 14-19. The temporal pattern of plasma miRNA is shown in FIGS. 4-8. Fold change was shown relative to miRNA levels from age matched normal subjects. Levels of miRNA were normalized using measured levels of snRNA U6 (used as a standard control). Quantitative PCR results for snRNA U6 are shown in FIG. 11. Statistical analysis of the results is shown in FIG. 13.

A unique temporal pattern of miRNAs occurred in post-MI patients including changes in miRNAs previously shown to regulate myocardial growth, fibrosis, and remodeling. Thus, serially profiling miRNAs in the plasma of post-MI patients can be used to diagnose, assess, and monitor remodeling in patients.

Figure 9:
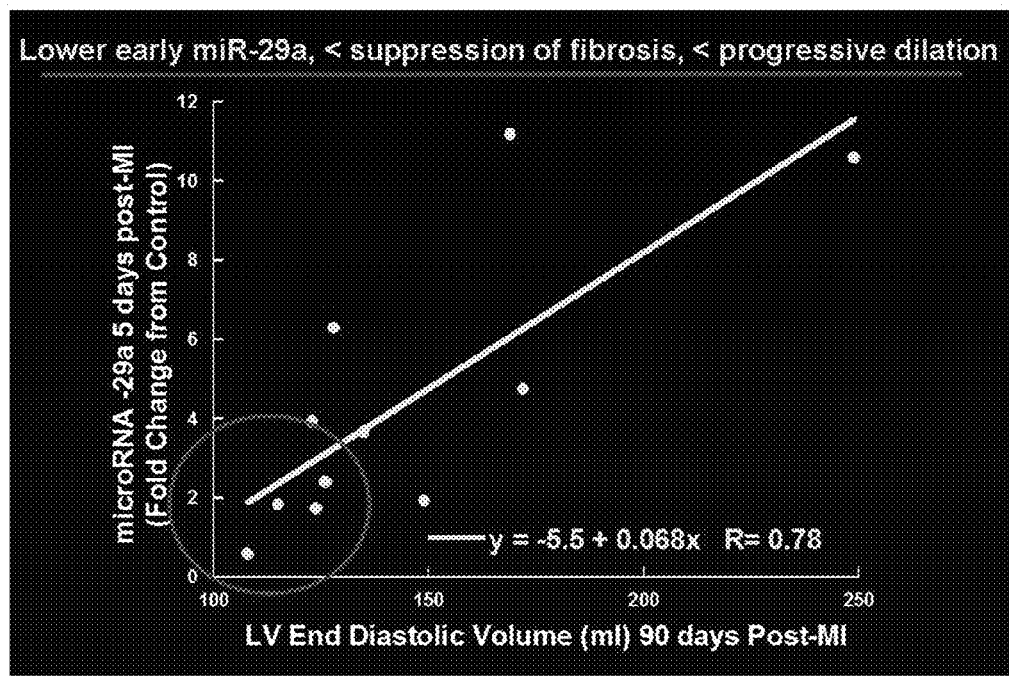
FIG. 9 is a graph of the fold change of microRNA-29a (compared to age matched normals) at 5 days after myocardial infarction versus left ventricular end diastolic volume at 90 days after myocardial infarction. The level of microRNA-29a at 5 days after myocardial infarction is positively correlated to left ventricular end diastolic volume at 90 days after myocardial infarction.
Figure 10:
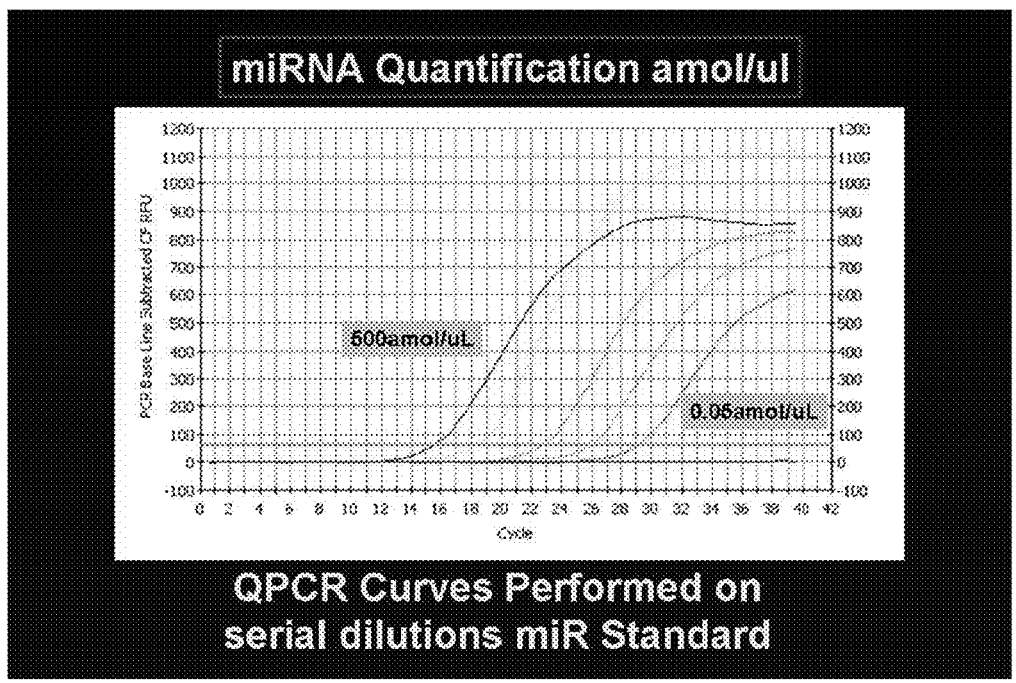
FIG. 10 is a graph of quantitative PCR (QPCR) production versus cycle number for various serial dilutions of an miRNA standard.

The results show that a unique temporal patterns of miR-NAs previously shown to regulate myocaridal growth, fibrosis, and remodeling are present and reliably detectable in post-myocardial infarction patients. The temporal patterns are correlated to the level and severity of left ventricular remodeling after myocardial infarction (FIG. 9) indicating that the disclosed methods can be used for detecting, diagnosing, monitoring, prognosing cardiac remodeling and assessing the effectiveness of treatments for myocardial infarction and remodeling.

C. Example 2

Relationship Between The Temporal Profile of Plasma microRNA and Left Ventricular Remodeling in Patients Following Myocardial Infarction 1. Summary MicroRNAs (miRs) are small noncoding RNAs that associate with target mRNAs, act as negative regulators of gene expression by promoting mRNA degradation or inhibiting translation, and play a regulatory role in myocardial growth, fibrosis, viability, and remodeling. Whether specific temporal changes in miRs occur in patients during the LV remodeling process that follows a myocardial infarction (post-MI) remains unknown. The current study shows that plasma miRs can be reliably measured in post-MI patients and that there is a relationship between temporal changes in specific miRs and post-MI LV structural remodeling.

LV end-diastolic volume (EDV) and plasma miRs (miR-1, -21, -29a, 133a, 208, quantitative rt-PCR, normalized for endogenous snRNA U6) were measured in referent controls (CTL n=6) and post-MI patients (n=12) from day 2 through day 90 post-MI. Following MI, EDV increased progressively compared to CTL; this was accompanied by time dependent changes in specific miRs. For example, miR-21 (inhibits apoptosis) initially fell 2 days post-MI increased 5 days post-MI and returned to CTL values at later time points. In contrast, miR-29a (inhibits changes in the extracellular matrix) increased 5 days post-MI and then fell to CTL. miR-208 (augments hypertrophy) increased 5 days post-MI and remained elevated.

In conclusion, a unique temporal pattern of miRs occurred in post-MI patients that included an early and robust rise in miRs that have been shown to affect myocardial growth, fibrosis and viability. Thus, serially profiling miRs in the plasma of post-MI patients can hold both mechanistic and prognostic significance.

2. Introduction

Left ventricular remodeling represents the aggregate effects of changes in cardiomyocytes, fibroblasts, and interstitial structure and function that result from cardiovascular disease processes such as a myocardial infarction. The molecular regulatory mechanisms that affect cellular and extracellular remodeling remain incompletely defined; however, recent studies suggest that microRNAs (miRs) may be one such mechanism (Divakaran V, Mann D L. The Emerging Role of MicroRNAs in Cardiac Remodeling and Heart Failure. *Circ Res.* 2008; 103:1072-1083; Small E M, Frost R J A, Olson E N. MicroRNAs Add a New Dimension to Cardiovascular Disease. *Circulation.* 2010; 121:1022-1032). MiRs are small noncoding RNAs (~22 nucleotides) that associate with target mRNAs and act as a negative regulator of gene expression by promoting mRNA degradation or inhibiting translation. Studies in animal models have suggested that miRs play a translational or post-translational regulatory role in myocardial growth, fibrosis, viability, and remodeling (Liu et al. microRNA-133a regulates cardiomyocyte proliferation and suppresses smooth muscle gene expression in the heart. *Genes Dev.* 2008; 22(23):3242-54; Duisters et al. miR-133 and miR-30 Regulate Connective Tissue Growth Factor. Implications for a Role of MicroRNAs in Myocardial Matrix Remodeling. *Circ Res.* 2009; 104:170-178; van Rooij et al. Dysregulation of microRNAs after myocardial infarction reveals a role of miR-29 in cardiac fibrosis. *Proc Natl Acad. Sci.* 2008; 105(35):13027-32; Dong et al. MicroRNA Expression Signature and the Role of MicroRNA-21 in the Early Phase of Acute Myocardial Infarction. *J Biol. Chem.* 2009;

284(43):29514-25; Roy et al. MicroRNA expression in response to murine myocardial infarction: miR-21 regulates fibroblast metalloprotease-2 via phosphatase and tensin homologue. *Cardiovasc Res.* 2009; 82(1):21-9). For example, miR-1 have been suggested to blunt LV hypertrophy, augment apoptosis and facilitate progressive dilation, miR-208 augments hypertrophy and increases the extracellular matrix, miR-21 and miR-133a inhibit apoptosis and miR-29a inhibits changes in the extracellular matrix.

Whether specific temporal changes in miRs occur in patients during the LV remodeling process that follows a myocardial infarction (post-MI) remains unknown. It is impractical to assess serial changes in miRs in post-MI patients using repetitive LV myocardial tissue biopsies; however, this can be done using plasma sampling. Accordingly, the current study disclosed herein developed a sensitive, reliable method to measure miRs in plasma in referent control subjects and post-MI patients, and to measure serial changes in specific miRs following an MI to determine whether there is a relationship between temporal changes in specific miRs and LV structural remodeling in post-MI patients.

3. Methods
   i. Protocol

Twelve patients with a confirmed MI (Post-MI) and 6 referent age-matched control subjects (CTL) were enrolled in this study after providing informed consent. All of the studies described herein were reviewed and approved by the Medical University of South Carolina Institutional Review Board.

For the MI patients, studies were performed beginning at the time of enrollment (post-MI day 1). Plasma from a peripheral vein blood sample was used to measure miR profiles at post-MI days 2, 5, 28, and 90. At post-MI days 1, 5, 28, and 90 an echocardiogram was obtained. For the referent control subjects, an echocardiogram and plasma sample was performed once at the time of enrollment. All subjects fasted overnight before each study but took their morning medications as prescribed.

Transthoracic echocardiography was performed using a Sonos 5500 system with an S-4 MHz transducer (Agilent Technologies, Andover, Mass.). Measurements were made with American Society of Echocardiography criteria.

ii. Subjects

Twelve patients with a confirmed MI and 6 referent age-matched control subjects were enrolled in this study. An ECG and/or a positive cardiac enzyme panel confirmed the MI. Patients were excluded from enrollment if there was a history of a previous MI; previous coronary revascularization surgery within past 24 months; a history of active malignancy; significant renal or hepatic dysfunction; active rheumatological disease. MI patient were treated according to AHA/ACC guidelines. The referent control group consisted of subjects with no evidence of cardiovascular disease. Cardiovascular disease was excluded by performing a complete medical history, comprehensive physical examination, ECG, and echocardiogram.

By experimental design there were no differences in age between referent control and post-MI patients (Table 3). The ratio of men to women was higher in the post-MI group. Heart rate and blood pressure were comparable between groups. Differences in medications reflect expected ACC/AHA guideline based protocols for post-MI patients. In the referent control subjects, β-adrenergic blockers, angiotensin-converting enzyme inhibitors, and angiotensin receptor antagonists were used to treat mild increases in systolic pressure. Aspirin or anti-inflammatory agents were used for management for arthritic pain.

TABLE 3

Demographics for Referent Control Subjects and Myocardial Infarction Patients

|  | Control | MI |
|---|---|---|
| Number 6 | 12 | |
| Age (years) | 59 ± 2 | 58 ± 3 |
| Males | 2 (33%) | 9 (75%) * |
| Body Surface Area (m2) | 1.87 ± 0.03 | 1.99 ± 0.04 |
| Heart Rate (bpm) | 70 ± 1 | 68 ± 2 |
| Arterial Systolic Pressure (mmHg) | 126 ± 4 | 119 ± 4 |
| Arterial Diastolic Pressure (mmHg) | 75 ± 3 | 67 ± 3 | iii. Plasma miRNA Measurements

Small RNAs from plasma were isolated using the mirVana PARIS Kit (AM1556, Ambion) which is based upon a denaturing/phenol chloroform extraction approach. Briefly, 400 μL of plasma was added to an equal amount of denaturing solution, and incubated on ice for 5 minutes. Following which, 800 μL of an acid-phenol chloroform solution was added to the samples in order to inactivate RNAases and to create an aqueous RNA phase. This aqueous phase was removed, and passed through glass-fiber filters binding the RNA. The RNA was then eluted using a low ionic-strength solution, yielding a final volume of 100 pt. Then, 11.4 μL was reversed transcribed into cDNA (Applied Biosystems TaqMan MicroRNA RT Kit #4366579) using pre-specified miR sequences for: miR-1, miR-29a, miR-133a, miR-21, miR-208, and snRNA U6 (Table 1). Next, 12.5 μL of the cDNA was preamplified (TaqMan PreAmp Master Mix Kit #4391128, Applied Biosystems) as well as the pooled miR primers. Finally, the preamplification product was subjected to real time PCR(CFX96 Real-Time System, BioRad). The relative cycle threshold (Ct) values for U6 snRNA were used as endogenous controls for normalizing the respective miR Ct values (Li et al. Real-Time Polymerase Chain Reaction MicroRNA Detection Based on Enzymatic Stem-Loop Probes Ligation. Anal Chem. 2009 Jul. 1; 81(13): 5446-51) and were calculated as dCt (dCt=miRNA Ct−snRNA U6 Ct). Changes in miRNA were reported as a fold change from referent control calculated as $FC=2^{\wedge(dCt\ post\ MI - dCt\ referent\ control)}$. These normalized Ct values were computed for each sample, and these measurements were performed in duplicate. Referent control values were set at 1.0. Therefore, in post-MI patients fold change values less then 1.0 represented a fall in miRNA expression and fold change values greater then 1.0 represented an increase in miRNA expression compared to referent control. In initial assays performed in triplicate using referent control samples, the coefficient of variation for individual miR values was less than 10% (Table 2).

TABLE 1

Applied Biosystems miRNA primers
(SEQ ID NOs: 1 to 16)

| miRNA | Catalog Number | Target Sequence |
|---|---|---|
| miR-1 | 2222 | UGGAAUGUAAAGAAGUAUGUAU |
| miR-21 | 0397 | UAGCUUAUCAGACUGAUGUUGA |
| miR-29a | 2112 | UAGCACCAUCUGAAAUCGGUUA |
| miR-133a | 2246 | UUUGGUCCCCUUCAACCAGCUG |
| miR-208a | 0511 | AUAAGACGAGCAAAAAGCUUGU |

TABLE 1-continued

Applied Biosystems miRNA primers
(SEQ ID NOs: 1 to 16)

| miRNA | Catalog Number | Target Sequence |
|---|---|---|
| U6 snRNA | 1973 | GUGCUCGCUUCGGCAGCACAUA UACUAAAAUUGGAACGAUACAGA GAAGAUUAGCAUGGCCCCUGCG CAAGGAUGACACGCAAAUUCGUG AAGCGUUCCAUAUUUUUACUGCC CUCCAUGCCCUGCCCCACAAACG CUCUGAUAACAGUCUGUCCCUGU CUCUCUCCUGCUGCUCCUAUGGA AGCGAAGUUUUCCGCUCCUGCAG AAAGCAAAGUUACGACUCAGAGAC GGCUGAGGAUGACAUCAGCGAUG UGC |

TABLE 2

Ct Values and Coefficient of Variation for Referent Controls

| miRNA | Ct Values (Mean ± SEM) | Coefficient of Variation (%) |
|---|---|---|
| miR-1 | 30.62 ± 0.38 | 2.80% |
| miR-21 | 22.77 ± 0.20 | 8.18% |
| miR-29a | 25.44 ± 0.52 | 9.29% |
| miR-133a | 30.62 ± 0.31 | 4.54% |
| miR-208a | 36.54 ± 1.65 | 5.08% |
| U6 snRNA | 30.00 ± 0.45 | 3.8% |

Five miRs and one endogenous control were chosen for this study. A representative miR was chosen to target a translational or post-translational molecular regulatory role in each aspect of post-MI remodeling including augmenting or inhibiting hypertrophy, extracellular matrix changes, apoptosis, and progressive dilation. miR-1 has been suggested to blunt LV hypertrophy, augment apoptosis and facilitate to progressive dilation, miR-208 augments hypertrophy and increases changes in the extracellular matrix, miR-21 and miR-133a inhibit apoptosis and miR-29a inhibits changes in the extracellular matrix.

iv. Data Analysis

The echocardiographic and miRNA data were presented in an untransformed manner using parametric statistics. Comparisons between CTL values and post-MI values were examined using a 2-way ANOVA for repeated measures in which CTL/Post-MI was the first treatment level and time after MI was the second treatment level. After the ANOVA, pair-wise comparisons were made using a Bonferroni method. The relationship between changes in miR levels and LV volumes in the post-MI period were examined by linear regression methods. Values of $p<0.05$ were considered significant. All values are presented as the mean and SEM. Statistical procedures were performed with Stata Statistical Software (Stata-Corp, release 8.0, College Station, Tex.). The authors had full access to the data and take full responsibility for their integrity. All authors have read and agree to the manuscript as written.

4. Results i. LV Structure

Figure 24:
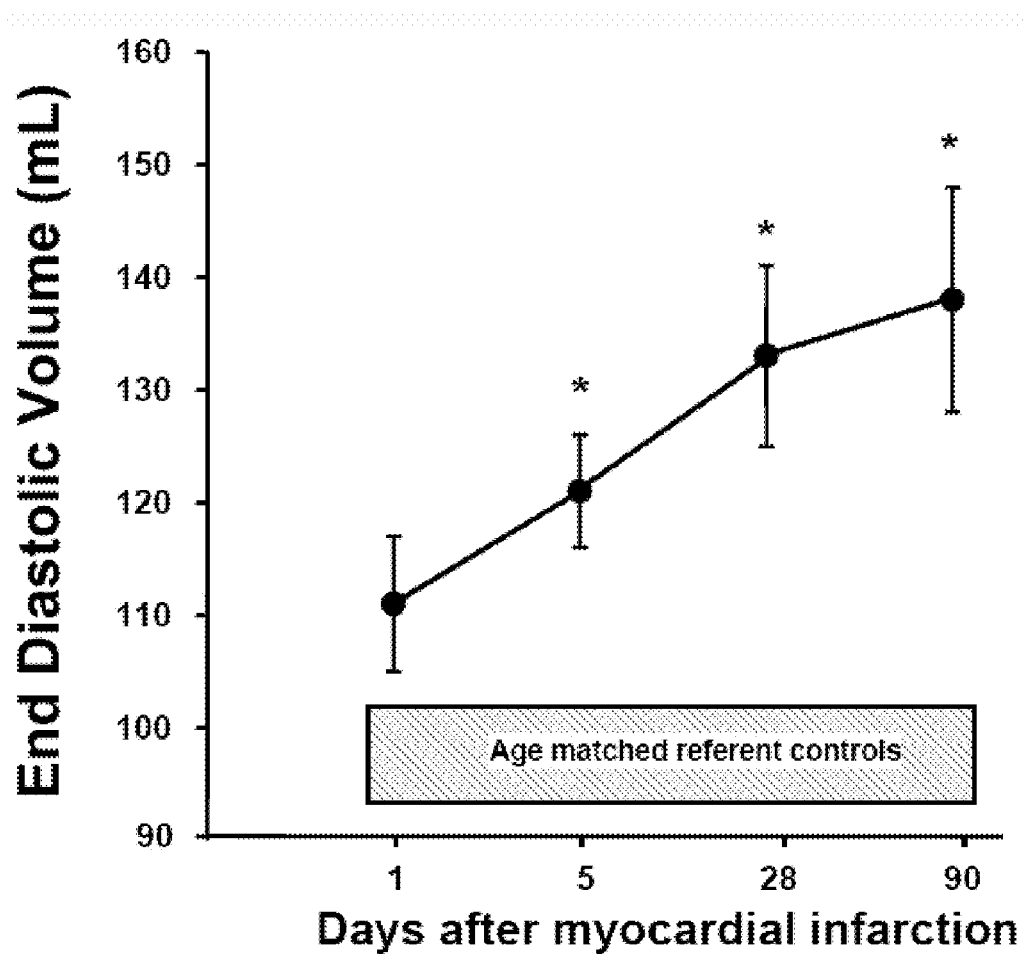
FIG. 24 shows that the end diastolic volume increased progressively following a myocardial infarction (closed circles) compared with referent controls (shaded box=normal range). *p<0.05 vs. controls.

LV end-diastolic volume increased in a time-dependent manner in the post-MI group as shown in FIG. 24. LV end diastolic volume was already increased compared with referent control on day 1 post MI. LV end-diastolic volumes increased further from post-MI day 1 values at post-MI day 28 and 90.

ii. miR

Figures 25A, 25B:
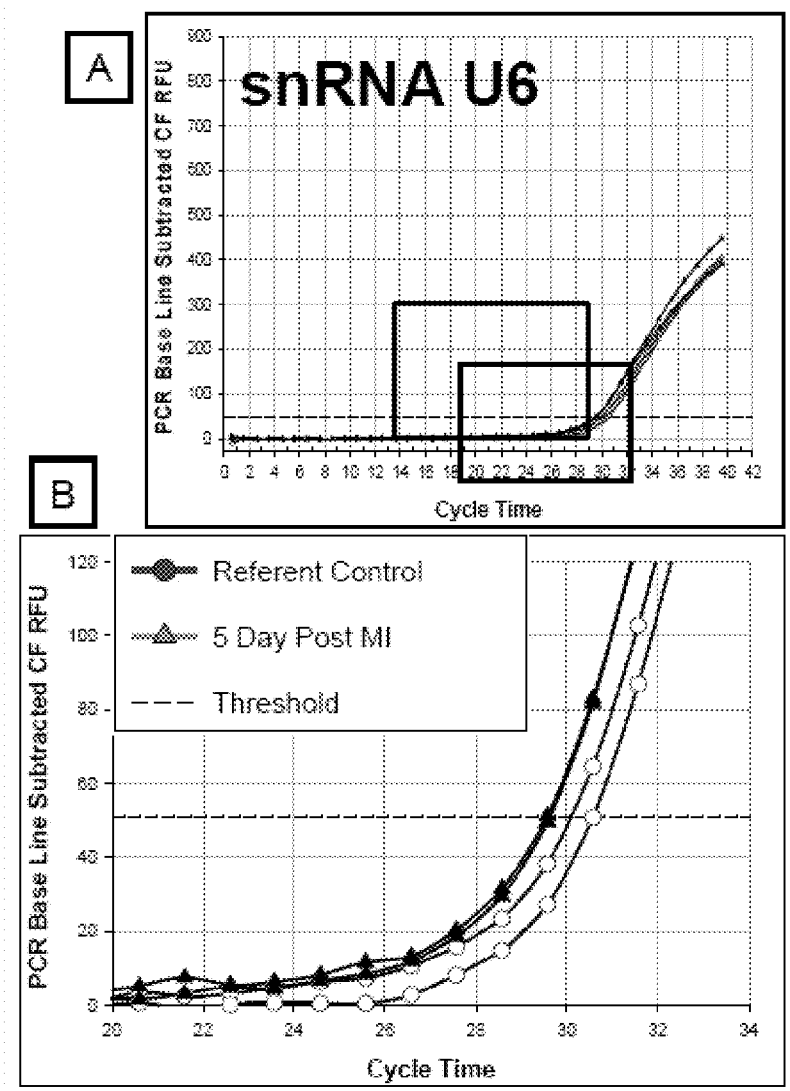
FIGS. 25A, 25B, 25C and 25D are examples of the quantitative real time Polymerase Chain Reaction (Qrt-PCR) in a referent control (CTL) versus a patient 5 days following a myocardial infarction (post-MI). snRNA U6 (panel A and B) expression (measured by cycle time) was not changed 5 days post MI. miR-1 (panel C and D) expression was increased 5 days post MI as evident by the reduction in cycle time from 30.7 in CTL to 28.1 for post-MI (arrow).
Figures 25C, 25D:
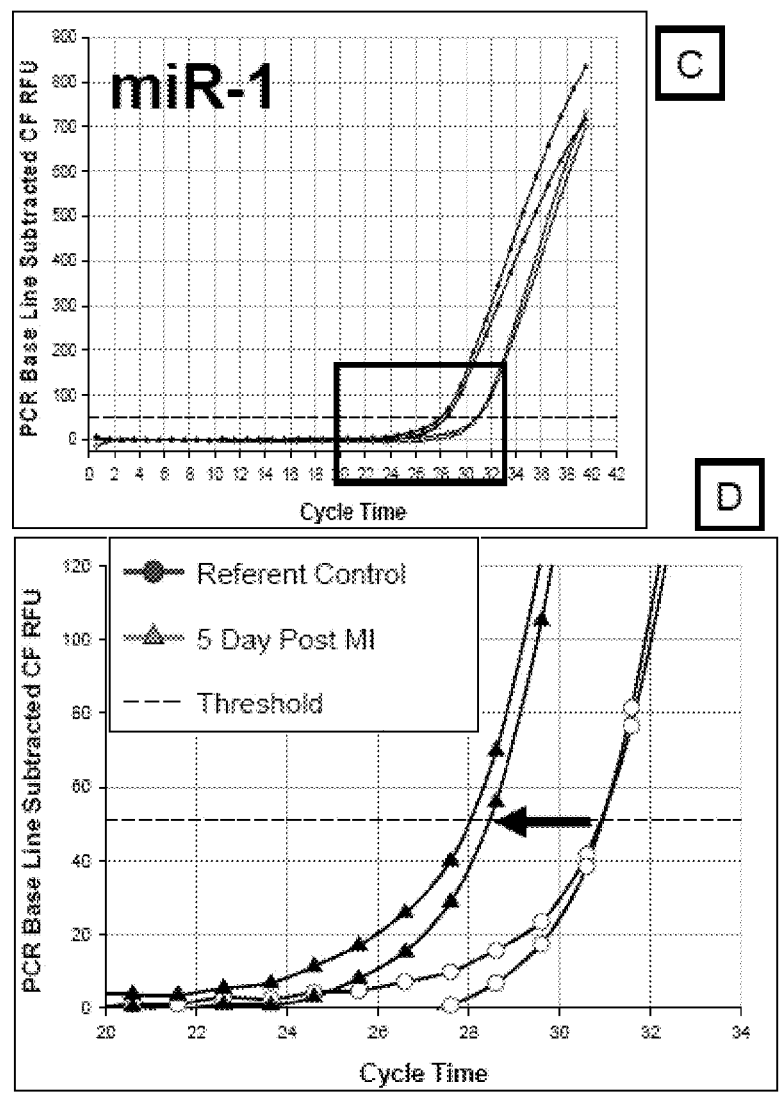
Figures 26A, 26B:
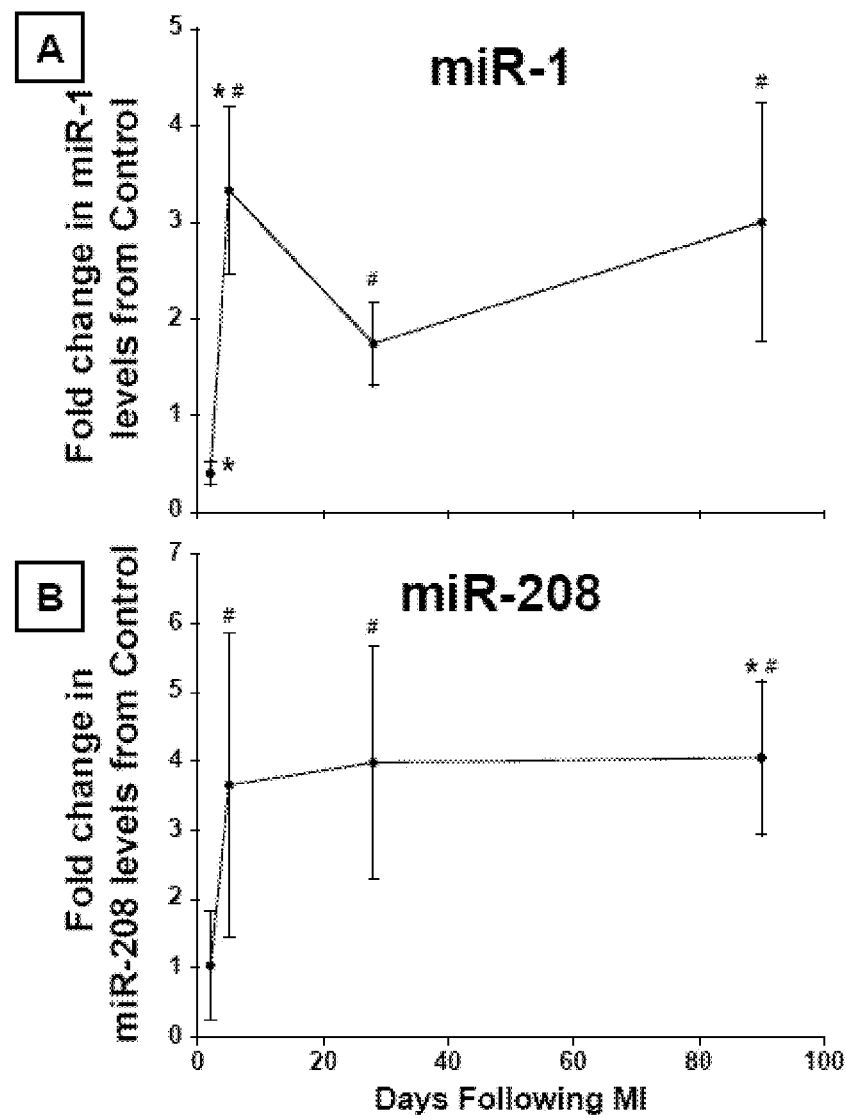
FIG. 26 shows serial changes in miRs following a myocardial infarction (MI). Post-MI data are presented as a fold change from controls (CTL) set at 1. *=P<0.05 vs. CTL; #=P<0.05 vs. day 2.
Figures 26C, 26D:
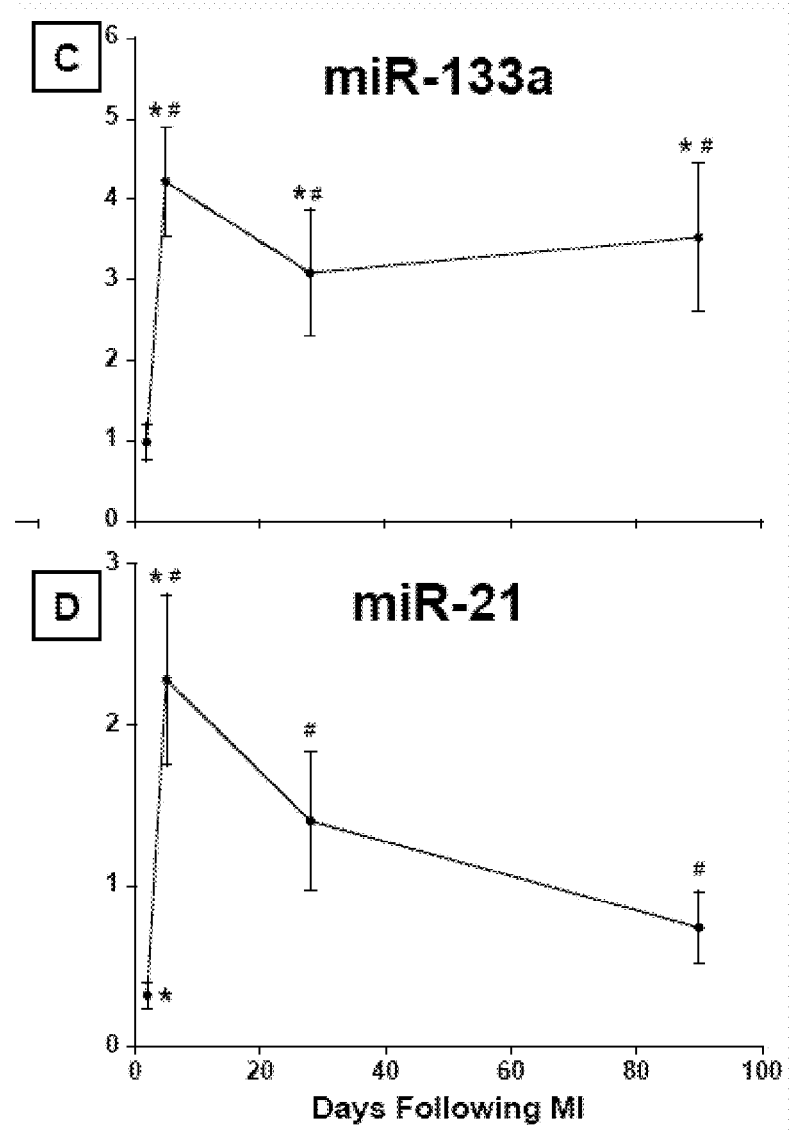

Examples of Qrt-PCR results for miR-1 and snRNA U6 in a referent control subject and an MI patient 5 days post MI are shown in FIG. 25. miR-1 expression was increased 5 days post MI as evidenced by a significant decrease in Ct from 31 in the referent control to 28 in the 5 day post MI patient. By comparison no change in snRNA U6 was seen post MI compared to referent control.

There were time dependent changes in the 5 measured miRs in the post MI patients compared to the referent control subjects (FIGS. 26-27). miR-1 and miR-21 fell at day 2 post MI, miR-29a, miR-133a and miR-208 were unchanged at day 2 post MI. miR-1, miR-133a, and miR-208 increased at day 5 and remained elevated through day 90 post MI. miR-21 and miR-29a were increased at day 5 but returned to normal by day 90 post MI.

Figure 27A:
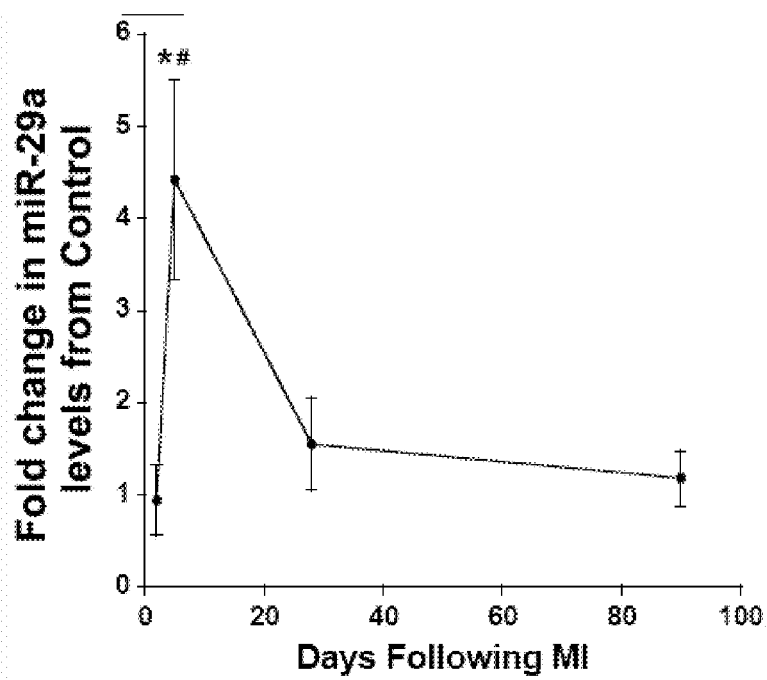
FIGS. 27A and 27B show changes in miR-29. Panel A shows serial changes in miR-29 (fold change from referent controls set at 1) following a myocardial infarction (MI). *=P<0.05 vs. CTL; #=P<0.05 vs. day 2. Panel B shows the relationship between early changes in miR-29a 5 days post-MI versus late changes in end diastolic volume 90 days post-MI. The larger the early increase in miR-29a at 5 days, the larger the late increase LV end diastolic volume following an MI. y=−5.5+0.07x, r=0.77.
Figure 27B:
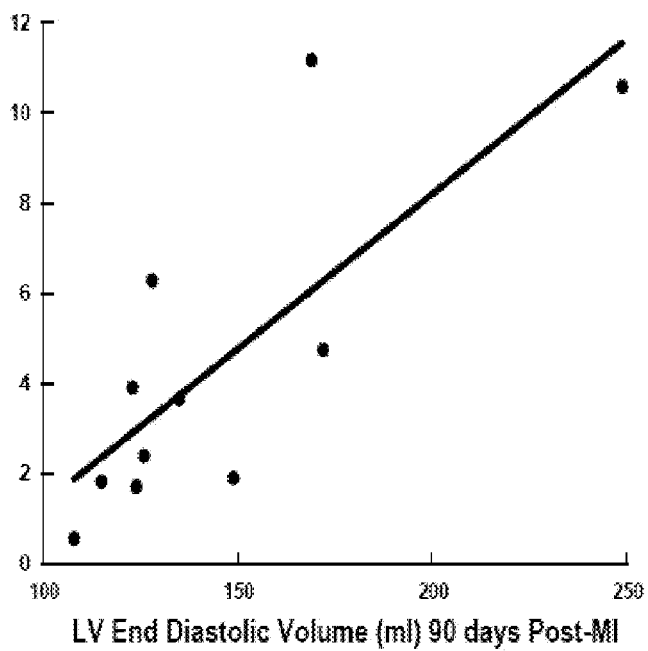

There was a significant association between miR-29a early after MI (post MI day 5) and LVEDV late after an MI (post Mi day 90), $r=0.77$ and $p<0.05$ (FIG. 27). The greater the increase in miR-29a at 5 days post MI, the greater the increase in LVEDV at 90 days post-MI.

5. Discussion

The principle finding in this study are three fold. First, miRs can be reproducibly measured in the plasma of patients following a myocardial infarction using a sensitive, reliable method. Second, differential miR expression occurred following a myocardial infarction, particularly in those miRs that are associated with myocardial growth, fibrosis and viability. Third, a unique temporal pattern of miRNAs occurred in post-MI patients. Therefore, serially profiling miRs in the plasma of post-MI patients can have both mechanistic and prognostic significance.

i. miR Processing and Function miRs are synthesized and processed in the nucleus, then transported into the cytoplasm and further processed into mature miRs (Divakaran V, Mann D L. The Emerging Role of MicroRNAs in Cardiac Remodeling and Heart Failure. Circ Res. 2008; 103:1072-1083; Small et al. MicroRNAs Add a New Dimension to Cardiovascular Disease. Circulation. 2010; 121:1022-1032). miRs associate with target mRNAs and act as negative regulators of gene expression by promoting mRNA degradation or inhibiting translation. Increased expression levels of miRs can also result in the "paradoxical" up regulation of previously suppressed target genes either directly, by decreasing the expression of inhibitory proteins and/or transcription factors, or indirectly, by inhibiting the expression levels of inhibitory miRs. Alternatively, decreased expression levels of inhibitory miRs can lead directly to increased target gene expression. Therefore, miRs are now believed to play a translational or post-translational regulatory role in myocardial growth, fibrosis, viability, and remodeling in response to cardiovascular disease.

ii. Plasma miRNAs

Given the fact that blood contains ribonucleases (RNases) it might be expected that neither serum nor plasma should contain any intact RNA. However, recent studies have demonstrated the presence of miRs in normal subjects and patients with disease (Mitchell et al. Circulating microRNAs as stable blood-based markers for cancer detection. Proc Natl Acad Sci USA. 2008; 105(30):10513-8; Chen et al. Characterization of microRNAs in serum: a novel class of biomarkers for diagnosis of cancer and other diseases. Cell Research. 2008; 18:997-1006). Further studies addressed the question of whether Qrt-PCR products found in plasma samples were the result of contamination by degraded products of large molecular weight RNA, tRNA, or genomic DNA. Studies indicate that there is a stable reproducible population of miR that exists in a form that is resistant to endogenase RNase, possibly because it is packaged inside an exosome or is associated with other molecules. For example, some of the total RNA isolated from human plasma was degraded by treatment with exogenous RNase, however, miRs were not degraded. miRs were not degraded by treatment with DNase, multiple freeze thaw cycles, prolonged incubation, or a large range of pH. However, when miRs, not homologous to human miR, were added to human plasma, these miRs were degraded. In patients with known cancer in whom tissue samples demonstrate an increase in specific miRs, the plasma has also been shown to have increased miRs.

iii. miRs and LV Remodeling

The role(s) of each miR in these processes remain controversial and incompletely defined; therefore assigning cause and effect relationships have not been firmly established. However, current information is based primarily on murine models of pressure-overload and MI, heterozygous or homozygous deletion of miR genes, use of antisense knockdown, and human myocardial samples of patients with end stage heart failure. What is clear from these studies is that miRs do contribute to the process of LV remodeling.

Studies have suggested that an increase in miR-1 and -133a may contribute to adverse remodeling by down regulating calmodulin and MEF2a and attenuating cardiomyocyte hypertrophy and fibrosis. As disclosed herein, increased miR-1 and -133a expression can contribute to the adverse LV remodeling consisting of progressive LV dilation that commonly follows an MI. An attenuation of both cardiomyocyte hypertrophy and a high rate of ECM turnover could contribute to this adverse remodeling process.

An increase in miR-21 may increase fibroblast survival, promote MMP-2 expression, increase collagen turnover and promote cardiomyocyte apoptosis. Disclosed herein, miR-21 was decreased at 2 days, increased at 5 days, and returned to normal after 5 days. This pattern reflects expected temporal pattern of changes in fibroblast number and activity following an MI, particularly within the infarcted myocardium.

miR-29a targets genes involved in ECM synthesis and turnover including collagens, fibrillins and elastin. Disclosed herein, miR-29a was increased 5 days post-MI a time during which the most rapid increase in LV volumes occurred, the interstitial matrix would have a high rate of turnover without significant establishment of mature structural fibrillar proteins. By contrast, miR-29a returned to normal at times later than 5 days post MI as disclosed herein and in previous studies of end stage ischemic cardiomyopathy, when fibrosis is significant, was found to be increased.

iv. Limitations

Quantitation of miR expression patterns using plasma sampling reflects global LV remodeling and can not be used to examine region specific changes in expression as would be possible for myocardial tissue samples. On the other hand, plasma samples do provide capability for serial measurements and provide temporal patterns not possible by myocardial tissue biopsy. In addition, plasma sampling provides an avenue for the use of miRs as diagnostic and prognostic biomarkers. For example, data from the study disclosed herein indicates that the extent of increased expression of miR-29a early post-MI is associated with the extent of remodeling late post-MI.

No cause and effect relationships between miR expression and changes in cellular and extracellular structure and function can be made based on the current studies. However, associations between miR temporal patterns and LV structural remodeling were detected.

D. Example 3

Plasma microRNA in Patients with Hypertensive Heart Disease: Differential Expression in Left Ventricular Hypertrophy Versus Diastolic Heart Failure MicroRNAs (miRs) are small noncoding RNAs that associate with target mRNAs and act as regulators of gene expression by promoting mRNA degradation or inhibiting translation. Animal models suggest that miRs play a translational or post-translational regulatory role in myocardial growth, fibrosis, and remodeling. This study demonstrates that specific miRs are differentially expressed in patients with LV hypertrophy (LVH) or diastolic heart failure (DHF). The results show that plasma miRs can be reliably measured in patients and that there is selective regulation of specific miRs with LVH vs. DHF.

1. Methods and Results

Figures 19, 20:
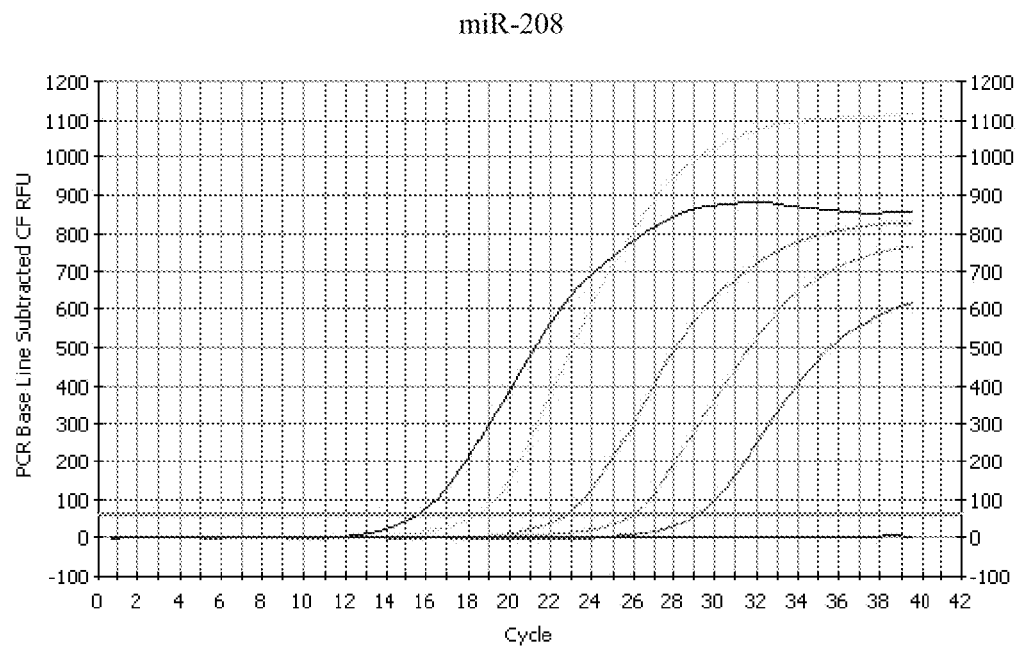
FIG. 19 is a graph of quantitative PCR production of miR-208 versus cycle number for various microRNA samples.
FIG. 20 shows an increase of miRs in patients with LVH compared to DHF.

Plasma miR, echocardiography, 6 minute hall walk (6 MHW) were measured in controls (CTL n=15) and patients with LVH but no DHF (n=13, LVH), and patients with LVH and DHF (n=13, DHF). DHF patients had shorter 6 MHW, increased pulmonary wedge pressures, and increased nt-proBNP compared with CTL or LVH patients. Selected miRs (miR-1, -21, -29a, 133a, 760) were measured using quantitative rt-PCR and normalized for endogenous snRNA U6 which served as a control (FIG. 20). Coefficient of variation for all miRs was less than 10%. In LVH, there were increases in miR-21 (augment hypertrophic growth), and increased miR-1, 29a, 133a, and 760 (limit fibrosis). In DHF, this compensatory response in miRs was lost; all miRs were similar to CTL possibly facilitating the increased fibrosis and less growth induction characteristic of DHF.

A unique profile of miRs was upregulated in patients with LVH; however, this compensatory response at the level of translational regulation was lost in patients who had developed DHF. See FIG. 20. Changes in miRs could serve as a novel biomarker identifying a molecular signature which reflects a change in translational regulation in patients making the transition from hypertrophy to heart failure.

E. Example 4

MicroRNA Profiling in Thoracic Aortic Aneurysm Disease: New Diagnostic and Mechanistic Insights MicroRNAs (miRs) are short non-coding RNAs that are endogenously expressed and function to inhibit gene expression through transcriptional and post-transcription mechanisms. While miR expression has been extensively studied in heart disease, their role in regulating gene expression during thoracic aortic aneurysm (TAA) development has yet to be explored. Accordingly, the present studied examined the expression level of seven miRs from patients with ascending TAAs that function to regulate multiple genes involved in aneurysm formation and progression.

MicroRNA was isolated from aortic tissue specimens, acquired at the time of surgical resection, from patients with ascending TAAs and tricuspid aortic valves (n=30). The relative expression levels of miR- (1, 21, 29a, 133a, 208, 486, and 760) were determined by quantitative real-time PCR. Results (mean±SEM) were expressed as a percent change from a cohort of normal aortic specimens (n=10) obtained from patients without aortic disease. See FIG. 21.

1. Results

Six of the seven miRs were expressed in the ascending thoracic aorta; the myocardial-specific miR-208 was not detected. A significant decrease (p<0.05 versus normal aorta, 100%) in the expression levels of miR-21, 29a, and 133a was demonstrated.

The unique findings from this study demonstrate altered miR expression patterns in clinical TAA specimens. The decreased miR expression in this study, suggests a loss of inhibitory control of genes regulating cellular growth/differentiation (miR-21), tissue remodeling (miR-29a, miR-133a), and cellular signaling (miR-133a). Altered miR profiles suggest that these miRs have relevance to the biological and clinical behavior of TAAs, and may prove to be useful as biomarkers for diagnostic or prognostic applications.

F. Example 5

The Human Myocardial Interstitium Contains a Specific Portfolio of microRNAs which are Dynamically Regulated Following Ischemia-Reperfusion MicroRNAs (miRs) regulate post-transcriptional events relevant to myocardial growth, viability and matrix remodeling (ie miR-1, -21, -29a, -133a. -486, -760). However, direct demonstration that miRs are released in a quantifiable manner within human myocardial interstitial fluid (INTf) and dynamically changed following ischemia-reperfusion (I/R) remained defined.

1. Methods and Results

Figures 21, 22:
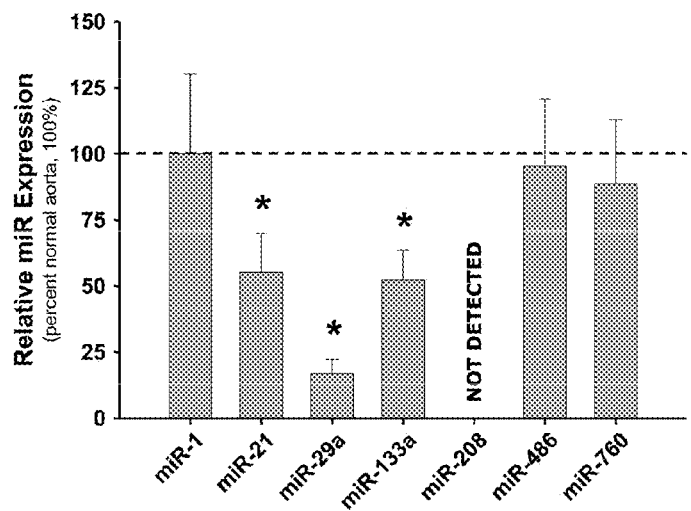
FIG. 21 is a graph of the relative expression levels of miRs determined by quantitative real-time PCR.
FIG. 22 shows a comparison of miRs in INTf and Plasma as well as the change following I/R.

Using novel microdialysis methods and high-sensitivity extraction, INTf was collected from the mid-myocardium of the LV free wall in patients (n=10, 63±3 yrs, male) undergoing elective coronary revascularization for the continuous collection of INTf prior to cardioplegic/myocardial arrest and cardiopulmonary bypass (Baseline) and following cross-clamp release and reperfusion (POST-I/R), with plasma collected at identical time points. See FIG. 22. Absolute miR content was determined by real-time PCR with a coefficient of variation of less than 10%; where a consistent yield of the constitutive miR-RNU6B was obtained from both INTf and plasma samples (31.9±0.4, 29.9±1.2 Ct, respectively). A robust Baseline miR concentration was detected in the INTf as well as plasma (FIG. 22). Higher levels of certain miRs (miR-1, -133a, -760) which regulate growth and signaling, were in the INTf-indicative of myocardial compartmentalization. Dynamic changes occurred in both INTf and plasma following I/R (Table), where selective miRs differentially changed within the INTf such as miR-1 and -760.

These unique findings demonstrated a robust expression of miRs which regulate myocyte and matrix remodeling within the human myocardial interstitium and dynamically change with I/R. In light of the fact that miRs form an important control point in transcriptional regulation, this study provides the first clinical evidence that miRs likely form a novel extracellular signaling/regulatory pathway within the intact human myocardium.

G. Example 6

High Frequency Electrical Stimulation of Human Myocardial Fibroblasts Causes Differential Expression of microRNAs Basic studies have established that micro RNAs (miRs) can regulate post-transcriptional processes relevant to myocardial remodeling. For example, miRs-21 and 29a have been suggested to regulate fibroblast growth and matrix remodeling. However, whether human left ventricular myocardial fibroblasts (LVMFs) specifically express these miRs and may be differentially regulated with specific stimuli had remained unclear. This study utilized primary human LVMFs in order to directly quantify miR-21 and 29a under steady-state conditions and following high frequency electrical stimulation.

1. Methods/Results

Figure 23:
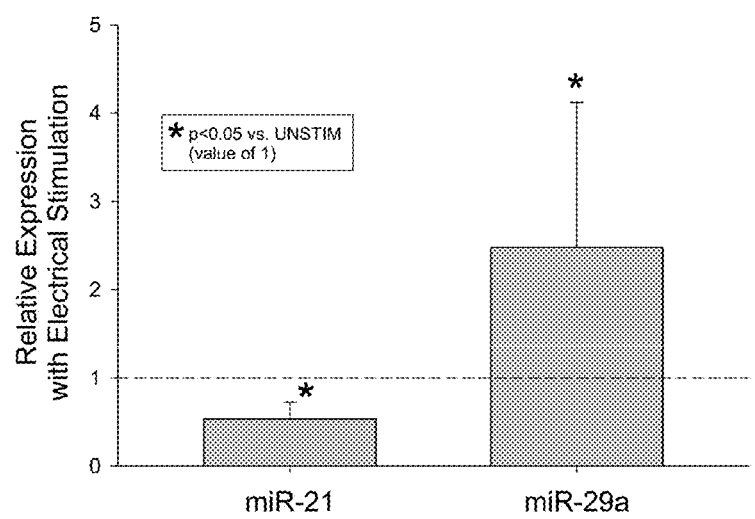
FIG. 23 is a graph showing that high frequency electrical stimulation of human myocardial fibroblasts causes differential expression of microRNAs.

LVMFs from patients with normal function (ejection fraction>=50%, n=5), were grown to 80% confluence. LVMFs were serum deprived for 24 hours, and then randomized to electrical stimulation ($6 \times 10^5$ cells/well, 100V 5 ms pulses) for 24 hours at 4 Hz (n=6 wells/frequency). See FIG. 23. Unstimulated cells from the same subjects (0 Hz, UNSTIM) served as controls. Electrical stimulation had no effect on LVMF viability. Expression levels of the constitutive miRs, snRNA U6B and U44, and miR-21 and miR-29a were determined by quantitative real-time PCR from LVMFs. There was high expression of U6B and U44 in LVMF, which were unaltered by stimulation (CT values U6B: 31±1 vs. 31±1 and U44: 32±1 vs. 32±1, respectively). Expression of miR-21 and -29a were normalized for levels of the constitutive miRs, and expressed as a fold change from UNSTIM (FIG. 23). With electrical stimulation, relative expression of miR-21 was lower while that of miR-29a was more than two-fold higher than UNSTIM (FIG. 23).

These unique findings of this study are two-fold: First, miR-21 and -29a are highly expressed in human LVMFs and appear to be differentially regulated by external stimuli. Second, human LVMFs respond to high frequency electrical stimulation through differential expression of miR-21 and -29a. These findings hold relevance to regulation of myocardial extracellular matrix remodeling.

REFERENCES

Chen X, Ba Y, Ma L, Cai X, Yin Y, Wang K, Guo J, Zhang Y, Chen J, Guo X, Qibin L, Li X, Wang W, Zhang Y, Wang J, Jiang X, Xiang Y, Xu C, Zheng P, Zhang J, Li R, Zhang H, Shang X, Gong T, Ning G, Wang J, Zen K, Zhang J, Zhang C. Characterization of microRNAs in serum: a novel class of biomarkers for diagnosis of cancer and other diseases. *Cell Research*. 2008; 18:997-1006.

Divakaran V, Mann D L. The Emerging Role of MicroRNAs in Cardiac Remodeling and Heart Failure. *Circ Res*. 2008; 103:1072-1083.

Dong S, Cheng Y, Yang J, Li J, Liu X, Wang X, Wang D, Krall T J, Delphin E S, Zhang C. MicroRNA Expression Signature and the Role of MicroRNA-21 in the Early Phase of Acute Myocardial Infarction. *J Biol. Chem*. 2009; 284(43): 29514-25.

Duisters R F, Tijsen A J, Schroen B, Leenders J J, Lentink V, van der Made I, Herias V, van Leeuwen R E, Schellings M W, Barenbrug P, Maessen J G, Heymans S, Pinto Y M, Creemers E E. miR-133 and miR-30 Regulate Connective Tissue Growth Factor. Implications for a Role of MicroRNAs in Myocardial Matrix Remodeling. *Circ Res*. 2009; 104:170-178.

Li J, Yao B, Huang H, Wang Z, Sun C, Fan Y, Chang Q, Li S, Wang X, Xi J. Real-Time Polymerase Chain Reaction MicroRNA Detection Based on Enzymatic Stem-Loop Probes Ligation. Anal Chem. 2009 Jul. 1; 81(13):5446-51.

Liu N, Bezprozvannaya S, Williams A H, Qi X, Richardson J A, Bassel-Duby R, Olson E N. microRNA-133a regulates cardiomyocyte proliferation and suppresses smooth muscle gene expression in the heart. *Genes Dev.* 2008; 22(23):3242-54.

Mitchell P S, Parkin R K, Kroh E V, Fritz B R, Wyman S K, Pogosova-Agadjanyan E L, Peterson A, Noteboom J, O'Briant K C, Allen A, Lin D W, Urban N, Drescher C W, Knudsen B S, Stirewalt D L, Gentleman R, Vessella R L, Nelson P S, Martin D B, Tewari M. Circulating microRNAs as stable blood-based markers for cancer detection. *Proc Natl Acad Sci* USA. 2008; 105(30):10513-8.

Roy S, Khanna S, Hussain S A, Biswas S, Azad A, Rink C, Gnyawali S, Shilo S, Nuovo G J, Sen C K. MicroRNA expression in response to murine myocardial infarction: miR-21 regulates fibroblast metalloprotease-2 via phosphatase and tensin homologue. *Cardiovasc Res.* 2009; 82(1):21-9.

Small E M, Frost R J A, Olson E N. MicroRNAs Add a New Dimension to Cardiovascular Disease. *Circulation.* 2010; 121:1022-1032.

van Rooij E, Sutherland L B, Thatcher J E, DiMaio M, Naseem R H, Marshall W S, Hill J A, Olson E N. Dysregulation of microRNAs after myocardial infarction reveals a role of miR-29 in cardiac fibrosis. *Proc Natl Acad. Sci.* 2008; 105(35):13027-32.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a microRNA" includes a plurality of such microRNAs, reference to "the microRNA" is a reference to one or more microRNAs and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps.

Those skilled in the art will recognize, or be able to ascertain using no more than routine experimentation, many equivalents to the specific embodiments of the method and compositions described herein. Such equivalents are intended to be encompassed by the following claims.

We claim:

1. A method comprising detecting one or more target microRNAs in a body fluid of a subject at a plurality of different times, wherein the temporal pattern of the level of the one or more target microRNAs indicates the presence, severity, or a combination of left ventricular remodeling in the subject.

2. The method of claim 1, wherein the presence, severity, or a combination of left ventricular remodeling in the subject is indicated by comparing the temporal pattern of the level of the one or more target microRNAs to one or more reference temporal patterns.

3. The method of claim 1 or 2, wherein the one or more microRNAs comprise one or more of miR-1, miR-21, miR-23a, miR-29a, miR-30, miR-133a, miR-150,miR-195, miR-199, miR-208, miR-214, and miR-125b.

4. The method of claim 1, wherein the one or more microRNAs comprise one or more of miR-1, miR-21, miR-29a, miR-133a, miR-208, and miR-125b.

5. The method of claim 1, wherein the one or more microRNAs comprise one or more of miR-1, miR-21, miR-29a, miR-133a, and miR-208.

6. The method of claim 1, wherein the body fluid is plasma.

7. The method of claim 1, wherein the plurality of different times comprises two or more times separated by 1, 2, 3, 4, 5, 10, 15, 20, 23, 24, 25, 26, 27, 28, 30, 35, 40, 45, 50, 55, 60, 62, 65, 70, 75, 80, 85, 86, 87, 88, 89, and 90 days.

8. The method of claim 1, wherein the plurality of different times comprises two or more times separated by 2, 3, 23, and 62 days.

9. The method of claim 1, wherein the level of the one or more target microRNAs comprises the measured level of the one or more target microRNAs normalized to the measured level of a reference RNA in the body fluid.

10. The method of claim 9, wherein the reference RNA is snRNA U6.

11. The method of claim 1, wherein the level of the one or more target microRNAs comprises the measured level of the one or more target microRNAs expressed as the fold difference of the measured level of the one or more target microRNAs to the measured level of the one or more target microRNAs in a reference subject.

12. The method of claim 11, wherein the level of the one or more target microRNAs in a reference subject is measured at the same time as the level of the one or more target microIRNAs is measured in the subject.

13. The method of claim 11, wherein the level of the one or more target microRNAs in a reference subject is measured at a different time than the level of the one or more target microRNAs is measured in the subject.

14. The method of claim 11, wherein the level of the one or more target microRNAs in a reference subject is a reference level.

15. The method of claim 1, wherein the level of the one or more target microRNAs comprises the measured level of the one or more target microRNAs normalized to the measured level of a reference RNA in the body fluid expressed as the fold difference of the normalized level of the one or more target microRNAs to the measured level of the one or more target microRNAs in the same body fluid of reference subject normalized to the measured level of a reference RNA in the body fluid of the reference subject.

16. The method of claim 1, wherein the plurality of different times comprises two or more times 1, 2, 3, 4, 5, 10, 15, 20, 25, 28, 30, 35, 40, 45, 50, 55, 60, 65, 70, 75, 80, 85, and 90 days following a known or suspected myocardial infarction in the subject.

17. The method of claim 1, wherein the plurality of different times comprises two or more times 2, 5, 28, and 90 days following a known or suspected myocardial infarction in the subject.

18. The method of claim 1, wherein the temporal pattern of the level of the one or more target microRNAs indicates that the subject suffered a myocardial infarction.

19. The method of claim 18, wherein the temporal pattern of the level of the one or more target microRNAs indicates how long ago the subject suffered the myocardial infarction.

* * * * *